US009208468B2

(12) United States Patent
Olson et al.

(10) Patent No.: US 9,208,468 B2
(45) Date of Patent: Dec. 8, 2015

(54) INVENTORY MANAGEMENT SYSTEM

(75) Inventors: Jeffrey C. Olson, Dallas, PA (US); James Leo Kilgallon, Forty Fort, PA (US); Al Bowers, Aspinwall, PA (US); Bruce Quayle, Pittsburgh, PA (US); Mark Douglas Donaldson, Pittsburgh, PA (US); Chris Stygar, Pittsburgh, PA (US)

(73) Assignee: InterMetro Industries Corporation, Wilkes-Barre, PA (US)

( * ) Notice: Subject to any disclaimer, the term of this patent is extended or adjusted under 35 U.S.C. 154(b) by 184 days.

(21) Appl. No.: 13/982,511

(22) PCT Filed: Feb. 7, 2012

(86) PCT No.: PCT/US2012/024078
§ 371 (c)(1),
(2), (4) Date: Jul. 30, 2013

(87) PCT Pub. No.: WO2012/109194
PCT Pub. Date: Aug. 16, 2012

(65) Prior Publication Data
US 2013/0310967 A1    Nov. 21, 2013

Related U.S. Application Data

(60) Provisional application No. 61/440,156, filed on Feb. 7, 2011.

(51) Int. Cl.
| G06F 7/00 | (2006.01) |
| G06Q 10/08 | (2012.01) |
| G07F 9/02 | (2006.01) |
| G07F 11/60 | (2006.01) |
| G07F 17/00 | (2006.01) |

(52) U.S. Cl.
CPC .............. *G06Q 10/087* (2013.01); *G07F 9/026* (2013.01); *G07F 11/60* (2013.01); *G07F 17/0092* (2013.01)

(58) Field of Classification Search
None
See application file for complete search history.

(56) References Cited

U.S. PATENT DOCUMENTS

| 5,651,596 A | 7/1997 | Carlson et al. |
| 2004/0144794 A1 | 7/2004 | Clarke |

(Continued)

FOREIGN PATENT DOCUMENTS

GB    2 327 668 A    2/1999

OTHER PUBLICATIONS

International Search Report and Written Opinion for PCT/US2012/024078, mailed May 23, 2012; ISA/US.

(Continued)

*Primary Examiner* — Yolanda Cumbess
(74) *Attorney, Agent, or Firm* — Harness, Dickey & Pierce, P.L.C.

(57) ABSTRACT

The present disclosure provides an inventory management system that offers significant improvement over existing systems by automating requests to restock inventory. The present disclosure details an inventory management system that provides real time visibility to stock levels and streamlines materials management activities, while addressing the issues of human resource misallocations, inaccurate inventory data management and related out of stock conditions. Moreover, the system of the present disclosure promotes a high level of confidence in inventory data that enables on-hand inventory levels to be reduced, thereby reducing costs and waste.

22 Claims, 24 Drawing Sheets

(56) References Cited

U.S. PATENT DOCUMENTS

| | | |
|---|---|---|
| 2005/0131578 A1 | 6/2005 | Weaver |
| 2005/0168345 A1* | 8/2005 | Swafford et al. .......... 340/686.1 |
| 2007/0000981 A1 | 1/2007 | Jacobs |
| 2007/0250413 A1 | 10/2007 | Godlewski |
| 2008/0117048 A1* | 5/2008 | Rachwalski et al. ....... 340/572.1 |
| 2008/0283531 A1 | 11/2008 | Clarke |
| 2010/0193538 A1 | 8/2010 | Clarke |
| 2010/0282840 A1* | 11/2010 | Henry ........................... 235/382 |
| 2011/0153466 A1 | 6/2011 | Harish et al. |

OTHER PUBLICATIONS

Pieter Wolbers: "Stock items on the run. A research into the new inventory system in the OR-complex of the Reinier de Graaf hospital", Mar. 1, 2007, XP055172532, http ://essay. utwente. nl/593/1 /scriptie_Wolbers. pdf.

Extended European Search Report for PCT/US2012/024078, mailed Mar. 10, 2015; EPO.

* cited by examiner

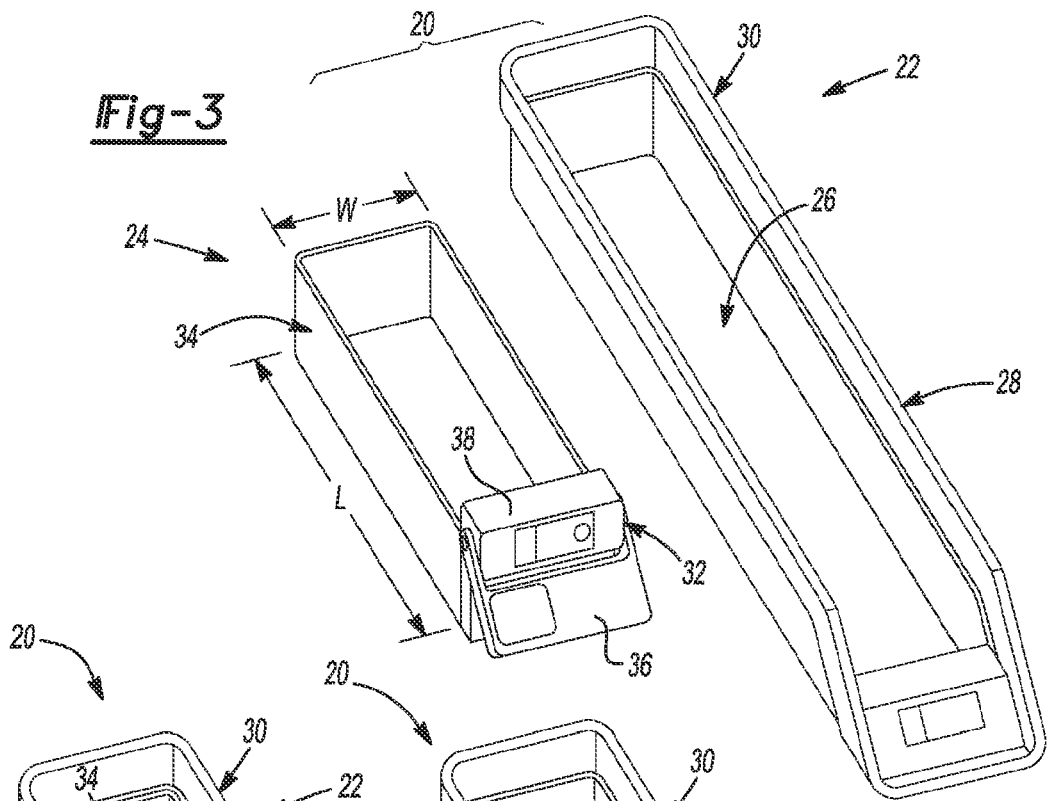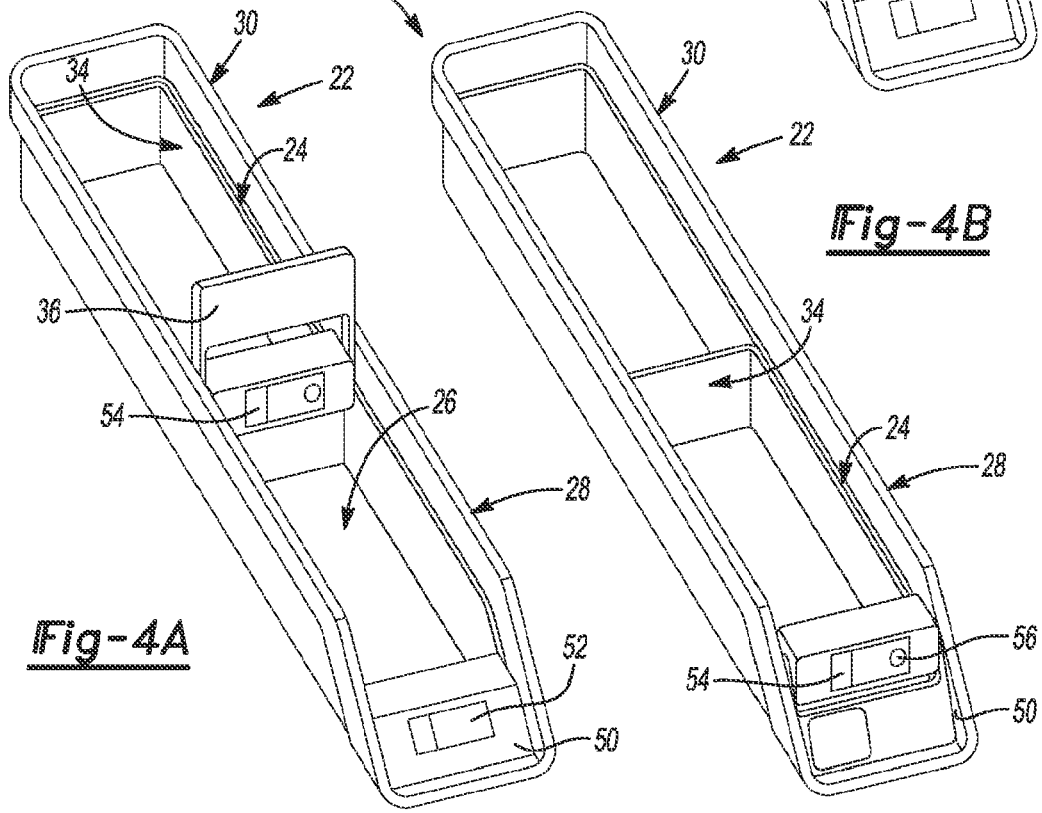

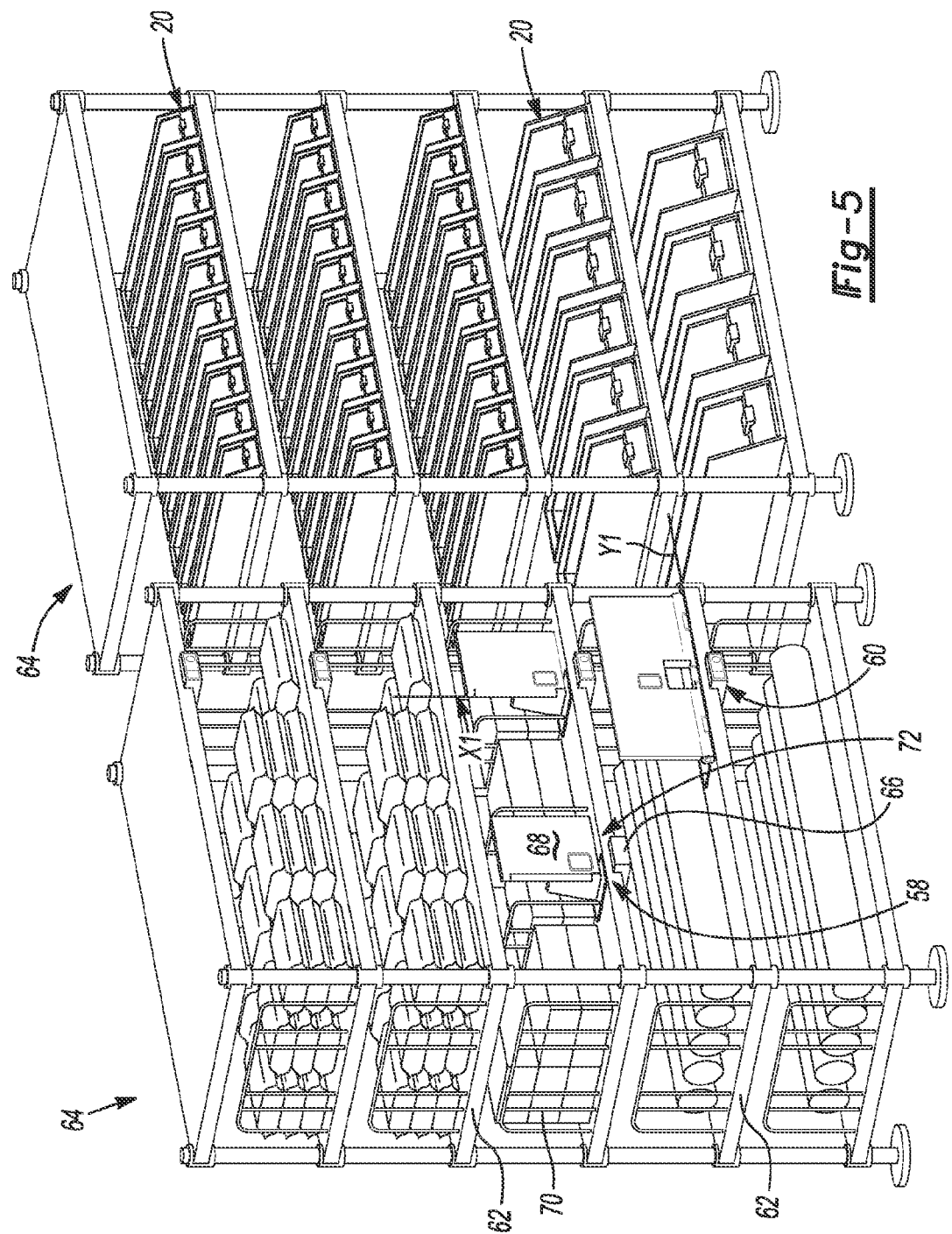

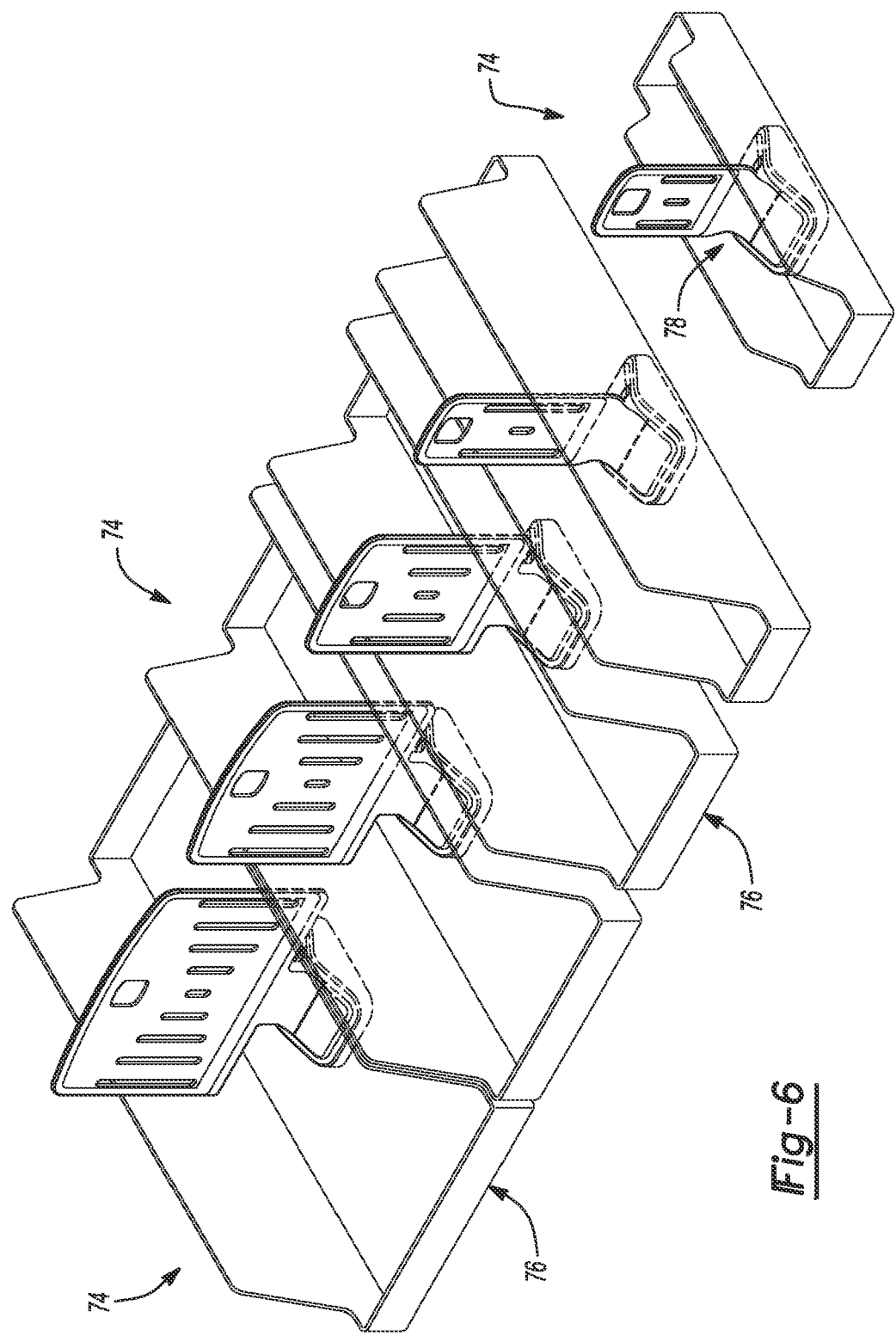

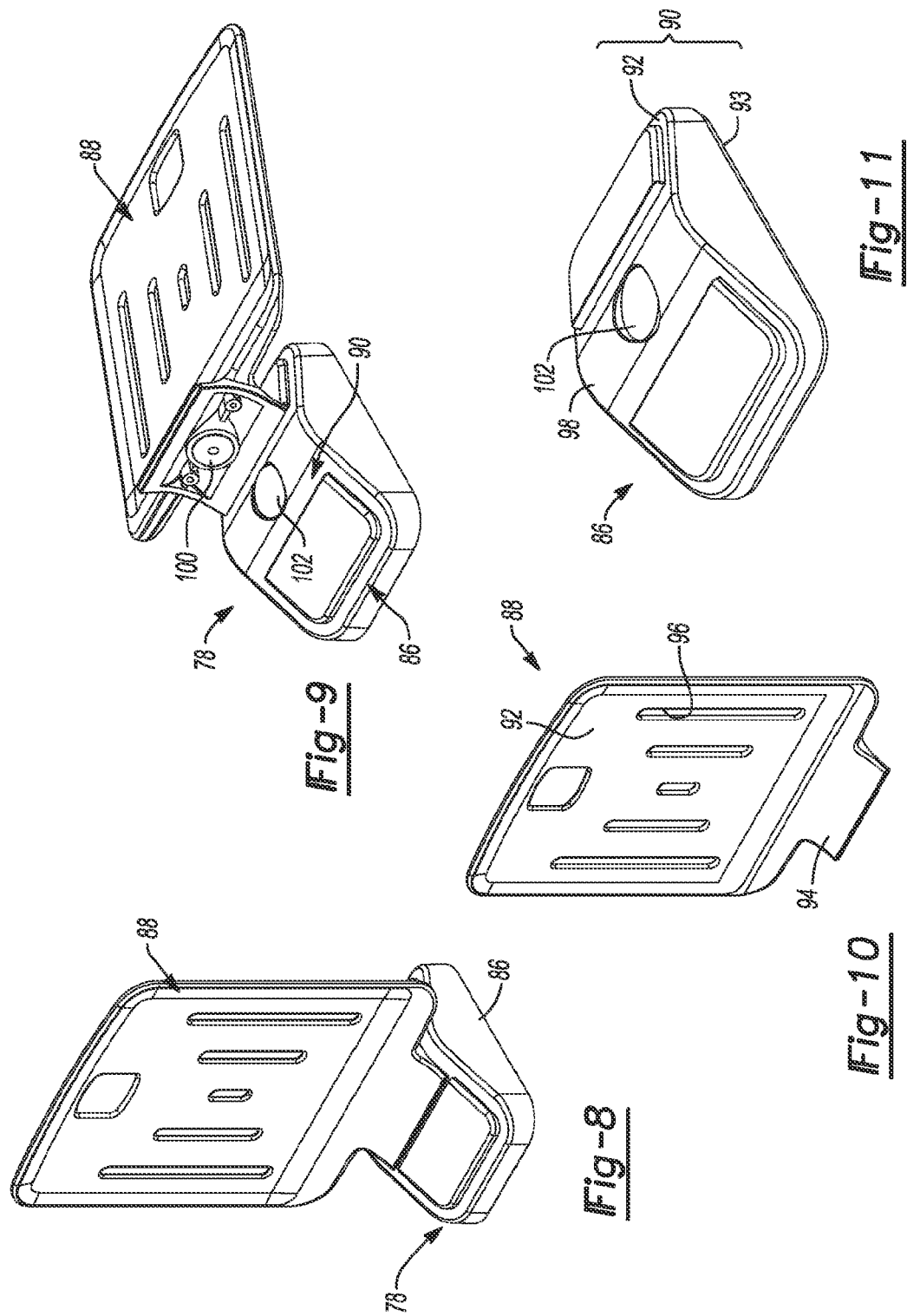

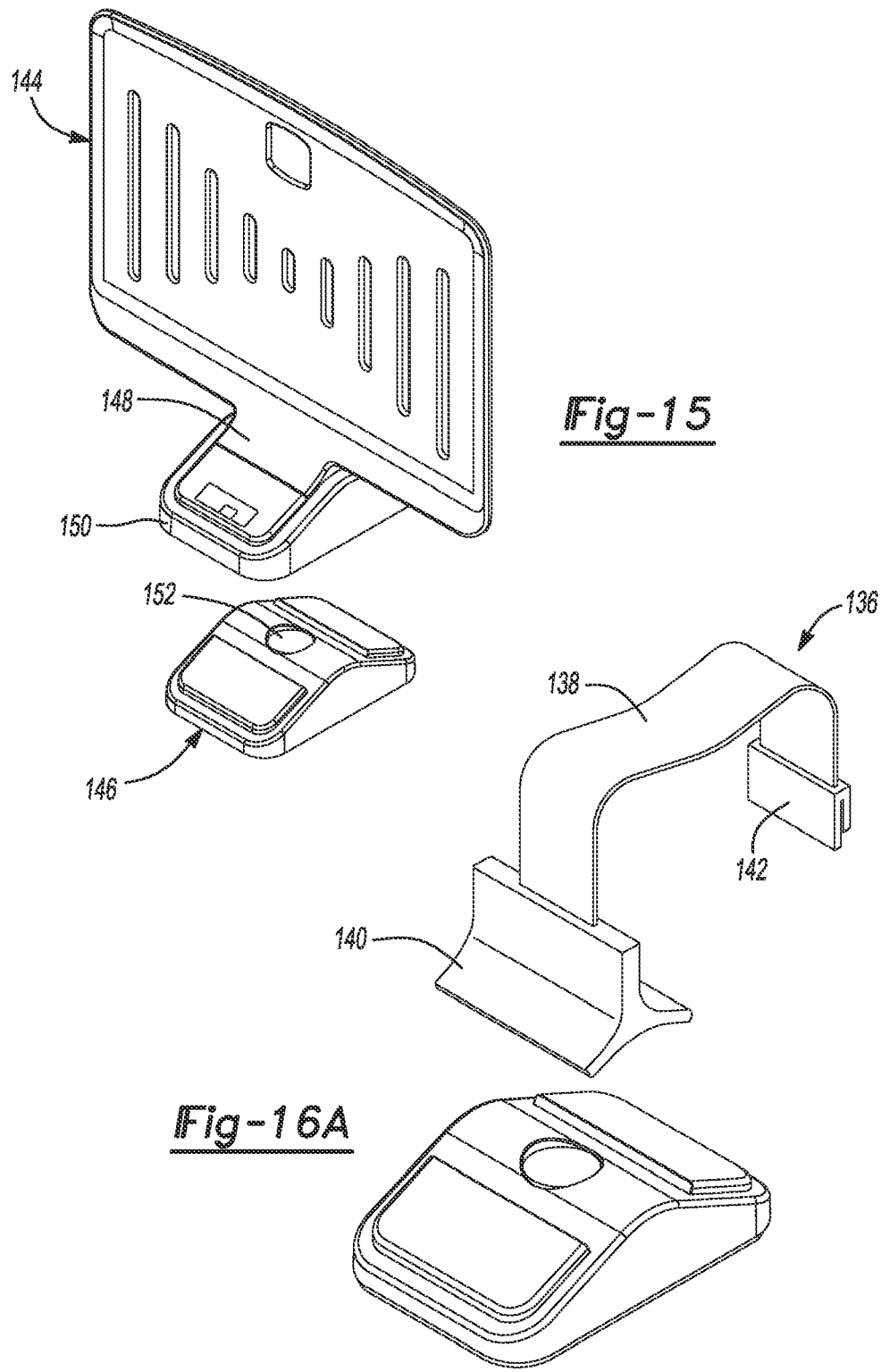

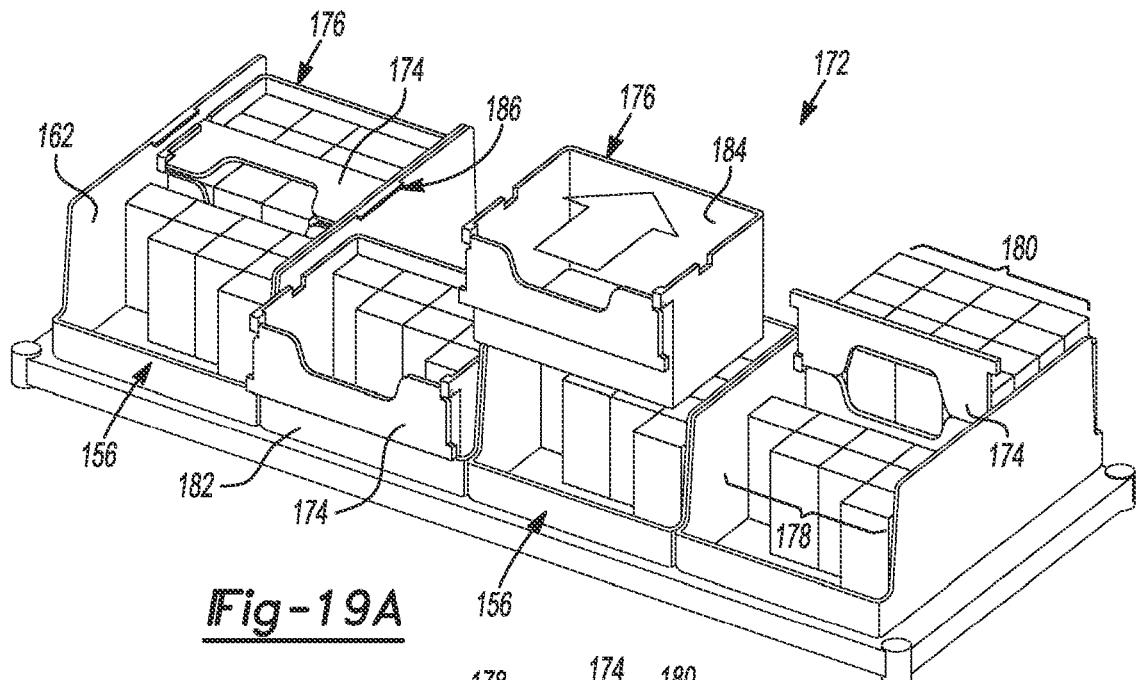
*Fig-19A*
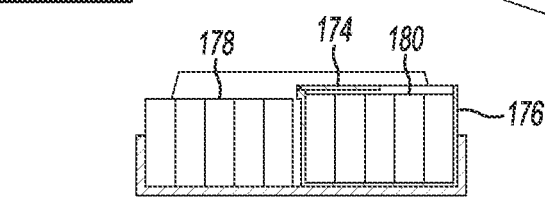
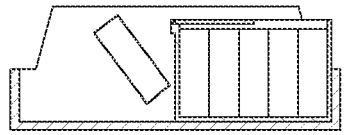
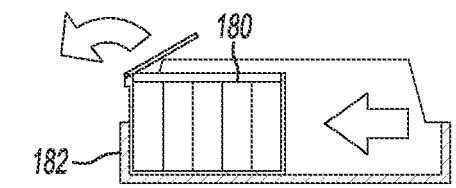
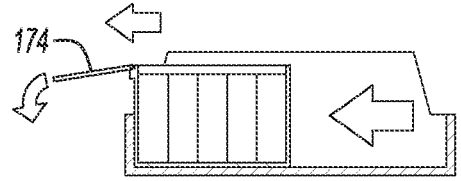
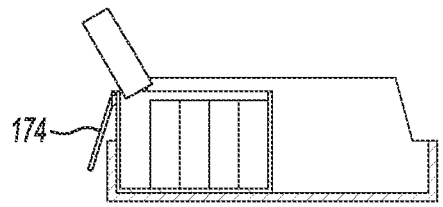
*Fig-19B*

INVENTORY MANAGEMENT SYSTEM

CROSS-REFERENCE TO RELATED APPLICATION

This application is a 371 National Stage of International Application No. PCT/US2012/024078, filed on Feb. 7, 2012, which claims the benefit of U.S. Provisional Application No. 61/440,156, filed on Feb. 7, 2011. The entire disclosures of the foregoing applications are incorporated herein by reference.

FIELD

The present disclosure relates generally to the field of materials management and, more particularly, to inventory management and control systems, including inventory storage apparatus, and methods for inventory data management and process control.

BACKGROUND

This section provides background information related to the present disclosure which is not necessarily prior art.

Materials management in healthcare facilities, like hospitals, is an important mechanism to help ensure that healthcare professionals have ready access to the supplies, medications and other materials that are required to serve the needs of their patients. In addition, such systems monitor inventories of supplies to help reduce waste and control supply costs.

Many hospitals and other healthcare facilities manage their inventory of supplies, medications and other materials using a "par-level" inventory control method (PAR). PAR inventory controls require stocking a predetermined quantity for each item in inventory, referred to as the 'par level." The par level may, for example, be based on an average usage of the item over a specific time period (e.g., 2-3 days), thus providing the quantity of items that is desired to be maintained on-hand. As the items are used, the number of items is replenished on a regular basis by taking a physical inventory of the items and then restocking the items to bring the on-hand inventory quantities "up to par." A PAR inventory control system seeks to avoid an out of stock condition by maintaining close control over inventory quantities.

Another method of inventory control used by hospitals and healthcare facilities is a Kanban system. As in a PAR inventory control system, a Kanban system establishes a target quantity for items to be maintained in on-hand inventory. However, instead of taking physical inventory and restocking item quantities on a regular basis over time to bring the quantities "up to par," a Kanban system establishes a fixed quantity of inventory depletion that triggers the restocking function. For example, in a "two-bin"-type Kanban system, two identical quantities of the inventory item are stocked in on-hand inventory, each quantity of items, however, is contained in a separate storage "bin." The on-hand inventory items are taken, as needed, from a first storage bin until that bin's inventory has been depleted. The depletion of inventory from the first storage bin, however, acts as a trigger for initiating the restocking of the on-hand inventory. As the first storage bin is restocked, then, the quantity of inventory items in a second storage bin satisfies the demand for that item. This cycle then repeats. Two-bin Kanban systems, therefore, offer simplicity and efficiency in managing the inventory of low cost supplies. And, unlike a PAR system, no physical inventory or counting of on-hand items is necessary.

In order to operate as intended and maintain the integrity of the inventory management system, however, both the PAR and Kanban methods described require significant user involvement, such as manually conducting regular physical inventories, manual data collection and recording activities, and manually placing of inventory restocking orders. Oftentimes, the operating protocols for these methods become unduly burdensome and time consuming to their users, whose primary work tasks involve the delivery of healthcare services and not inventory management. As such, these methods can foster an undesirable misallocation of human resources. Moreover, the amount of user involvement required by these systems provides opportunities for human error at any of several user interfaces to the systems which can negatively impact their function and efficiency. Other negative features associated with existing PAR and Kanban systems include the inability to ensure that the inventory is deplete in a "first in, first out" manner.

Prior efforts to automate aspects of the inventory management systems in an effort to alleviate some of the burdens placed on the systems' users, such as "weight-based systems" or "push-to-take systems" have proved ineffective and/or have manifested other undesirable features. For example, weight-based systems, which attempt to monitor on-hand inventory levels of stock items by employing scales to measure the weight of the bins containing the items, have high capital costs and require significant materials management operational capabilities. In addition, the reliability of such systems has proved less than desirable since there are many factors which can contribute to a false understanding of the inventory level, including calibration of the scales and variances in packaging for the same products which contribute to different weights for the same products. Push-to-take systems also exhibit noteworthy shortcomings. Push-to-take systems require that the user make a data entry (for example, by pushing a button on the storage bin) each and every time an item is removed from inventory. Consequently, such inventory management systems tend to have low user compliance rates which directly results in low data integrity for the system.

SUMMARY

This section provides a general summary of the disclosure, and is not a comprehensive disclosure of its full scope or all of its features.

The present disclosure provides an improved two-bin inventory management system that automates the restocking trigger resulting in significant improvement over existing two-bin systems by eliminating the necessity for healthcare professionals or materials management staff to initiate a request to restock inventory.

In one aspect of the present disclosure there is described an inventory management system comprising a storage module and a data reader module. In another aspect of the disclosure an inventory management system also comprises an inventory data management module. In yet another aspect of the present disclosure is described an inventory management protocol.

In another aspect of the disclosure a system for managing an inventory of stock items includes a storage bin adapted to contain a plurality of a stock item that are segregated into a first quantity of the stock item and a second quantity of the stock item, the first quantity of the stock item being located at a first position in the storage bin and the second quantity being located at a second position in the storage bin; and a sleeve received within an interior space of the storage bin, the sleeve comprising a control portion and a containment portion; the control portion including a trigger that is movable between a first position and a second position, the control portion being operable to broadcast a radio frequency (RF) signal containing information relating to the identity or condition of the storage module; the containment portion comprising a wall-like perimeter structure without a bottom enclosure, the containment portion defining an interior volume and adapted to segregate the second quantity of the stock item from the first quantity of the stock item within the storage bin; and wherein the inventory storage module broadcasts a restocking request upon movement of the trigger; and an inventory data management module comprising a user interface, the inventory data management module facilitating the administration of the stock items in the inventory based upon the restocking request.

In another aspect of the disclosure a system for managing an inventory of stock items includes an inventory storage module comprising a storage bin adapted to contain a plurality of a stock item that are segregated into a first quantity of the stock item and a second quantity of the stock item, the first quantity of the stock item being located at a first position in the storage bin and the second quantity being located at a second position in the storage bin; and a sleeve received within an interior space of the storage bin, the sleeve comprising a containment portion comprising a wall-like perimeter structure without a bottom enclosure, the containment portion defining an interior volume and adapted to segregate the second quantity of the stock item from the first quantity of the stock item within the storage bin; and an inventory data management module comprising a user interface, the inventory data management module facilitating the administration of the stock items in the inventory.

In another aspect of the disclosure a system for managing an inventory of stock items includes an inventory storage module having a divider member attached directly to a shelf of a storage device that is adapted to hold a plurality of a stock item that are segregated into a first quantity of the stock item and a second quantity of the stock item, the first quantity of the stock item being located at a first position on the storage device and the second quantity being located at a second position on the storage device; the divider member comprising a base portion and a trigger device, the trigger device being pivotable between a first position where the trigger device obscures one of the first or second quantities of the stock item, and a second position; the base portion being operable to detect movement of the trigger and to broadcast a radio frequency (RF) signal containing information relating to the identity or condition of the storage module; and an inventory data management module comprising a user interface, the inventory data management module facilitating the administration of the stock items in the inventory based upon the identity or condition of the storage module.

In another aspect of the disclosure a system for managing an inventory of stock items includes an inventory storage module includes a storage bin adapted to contain a plurality of a stock item that are segregated into a first quantity of the stock item and a second quantity of the stock item, the first quantity of the stock item being located at a first position in the storage bin and the second quantity being located at a second position in the storage bin; a divider member received within an interior space of the storage bin, the divider member separating the first quantity of the stock item from the second quantity of the stock item, the divider member comprising a base portion and a partition portion, the partition portion comprising a trigger that is movable between a first position and a second position, the base portion being operable to detect movement of the trigger and to broadcast a radio frequency (RF) signal containing information relating to the identity or condition of the storage module; and an inventory data management module comprising a user interface, the inventory data management module facilitating the administration of the stock items in the inventory based upon the identity or condition of the storage module.

A method for operating a system for managing an inventory of stock items provides yet another aspect of the disclosure and includes associating a stock item with a specific storage location in a managed environment; dividing a plurality of a stock item into a first quantity and a second quantity; placing the first quantity of the stock item in a first position at the storage location; placing the second quantity of the stock item in a second position at the storage location; placing a restocking trigger in an initial position; removing items from the first quantity until the first quantity of the stock item is depleted; moving the restocking trigger toward a deployed position; moving the second quantity of the stock item to the first position; broadcasting a restocking request; and restocking the storage location by placing a third quantity of the stock item in the second position at the storage location.

Still another aspect of the disclosure relates to a method for operating a system for managing an inventory of stock items that includes associating a stock item with a specific storage location in a managed environment; dividing a plurality of a stock item into a first quantity and a second quantity; placing the first quantity of the stock item in a first position at the storage location; placing the second quantity of the stock item in a second position at the storage location; providing a visual indication that the quantity of stock is in an initial condition; removing items from the first quantity until the first quantity of the stock item is depleted; moving the second quantity of the stock item to the first position; providing a visual indication that the quantity of stock is in a restocking condition; and restocking the storage location by placing a third quantity of the stock item in the second position at the storage location.

A further another aspect of the disclosure relates to a method for operating a system for managing an inventory of stock items that includes associating a stock item with a specific storage location in a managed environment; dividing a plurality of a stock item into a first quantity and a second quantity; placing the first quantity of the stock item in a first storage module at a first position of the storage location, the first storage module comprising a first RFID tag; placing the second quantity of the stock item in a second storage module at a second position of the storage location, the second storage module comprising a second RFID tag; removing items from the first storage module until the first quantity of the stock item is depleted; moving the first storage module to a third position at the storage location associated with a RFID reader/antenna; reading the first RFID by the RFID reader/antenna; broadcasting a restocking request for the stock item; moving the second storage module to the first position; removing items from the second storage module until the second quantity of the stock item is depleted; placing a third quantity of the stock item in the first storage module; and placing the first storage module in the second position at the storage location.

In another aspect of the disclosure a system for managing an inventory of stock items includes a plurality of individual inventory storage modules that are arranged on a storage shelf, each storage module comprising a storage bin for containing inventory stock items and a passive RFID tag containing identifying information relating to the storage module; a RFID antenna/reader located on the storage platform at a location separate from the storage modules, the RFID antenna/reader operable to read the RFID tag information of a storage module when the storage module is placed in proximity to the RFID antenna/reader; and wherein the storage modules are configured in a two-dimensional array on the shelf, wherein a first row of the array comprises a plurality of first storage modules and a second row of the array comprises a plurality of second storage modules; wherein the storage modules in each column of the array contain the same stock item; and wherein the identifying information contained in the RFID tag for each of the storage modules in a particular column of the array is serialized with the other storage modules in that column of the array.

Still another aspect of the disclosure a system for managing an inventory of stock items includes a first storage module comprising a first storage bin containing a first quantity of a stock item, and a first RFID tag being associated with the first storage module and containing unique identifying information relating to the first storage module, the first storage module being located at a first position of a storage location; a second storage module comprising a second storage bin containing a second quantity of the stock item, and a second RFID tag being associated with the second storage module and containing unique identifying information relating to the second storage module, the second storage module being located a second position of a storage location; a RFID reader/antenna being located at a third position of storage location, the RFID reader/antenna being operable to read the identifying information associated with one of the first and second storage modules and broadcast a restocking request for the stock item when one of the first and second storage modules is placed in proximity to the third location; and one of a data reader module and a data management module that is operable to receive the restocking request.

The present disclosure details an inventory management system that provides real time visibility to stock levels and streamlines materials management activities, while addressing the issues of human resource misallocations, inaccurate inventory data management, first-in, first-out (FIFO) compliance, and related out-of-stock conditions. Moreover, the system promotes a high level of confidence in inventory data which enables on-hand inventory levels to be reduced, thereby reducing costs and waste.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 shows an exemplary embodiment of an inventory storage module for the inventory management system of the present disclosure FIG. 4A shows the inventory storage module of FIG. 3 in an initial or reset condition;

FIG. 4B shows the inventory storage module of FIG. 3 in a triggered, restocking condition;

FIG. 5 shows additional exemplary embodiments of inventory storage modules for the inventory management system of the present disclosure;

FIG. 6 illustrates several exemplary embodiments of yet another alternative inventory storage module for the inventory management system of the present disclosure;

FIG. 8 shows a divider member of the inventory storage module of FIG. 9;

FIG. 9 shows the divider member of FIG. 8 in a triggered condition;

FIG. 10 illustrates a panel of the divider member of FIG. 8;

FIG. 11 illustrates a base of the divider member of FIG. 8;

FIG. 15 illustrates another alternative exemplary embodiment of the divider member;

Figure 16C:
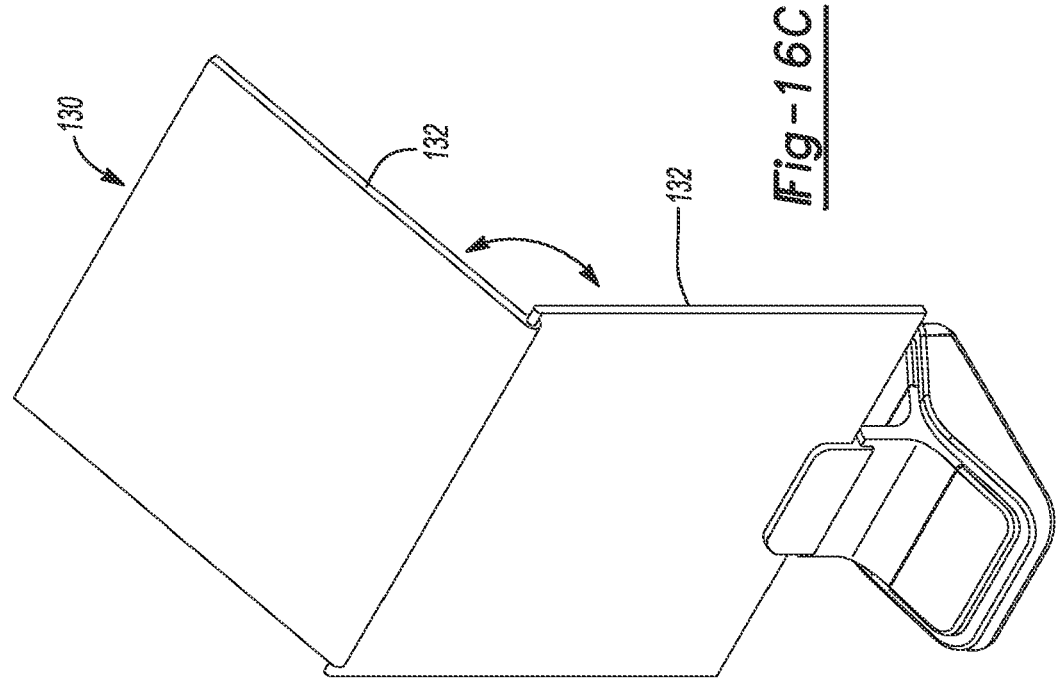
Figure 16B:
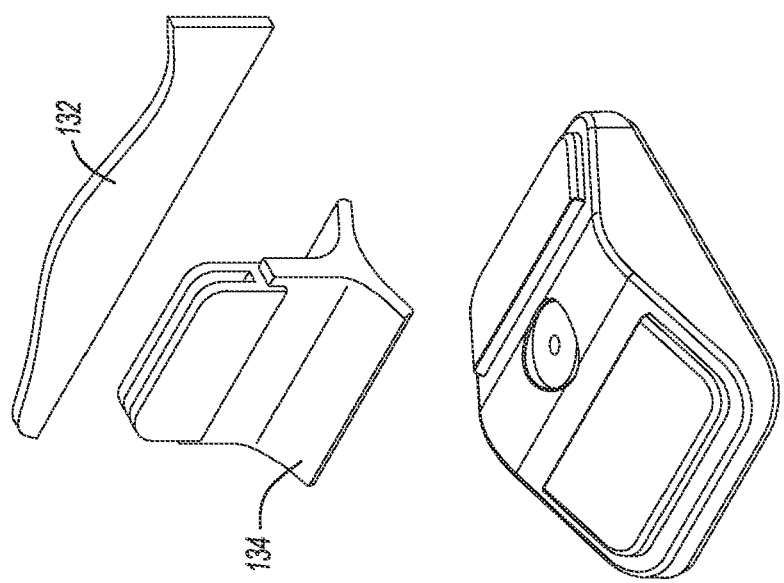

FIGS. 16A, 16B and 16C all show still further alternative exemplary embodiments of the divider member and partition portion.

Figure 17A:
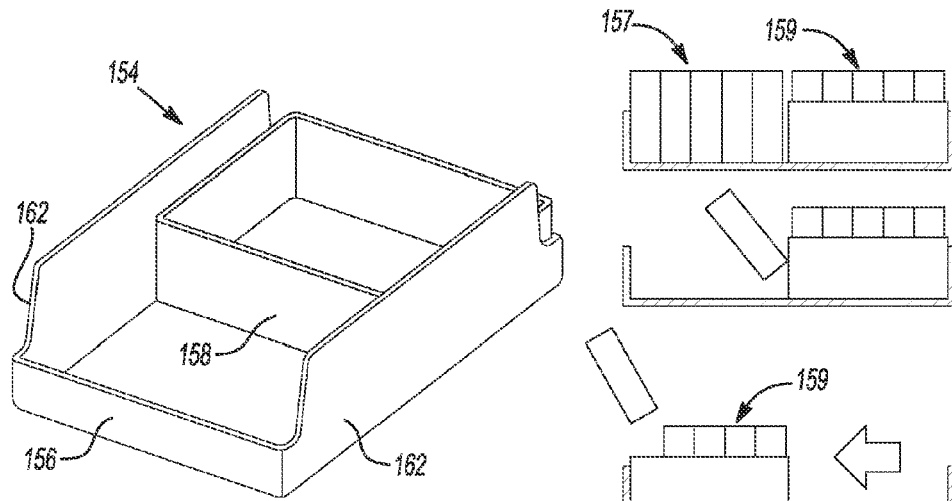
Figure 17B:
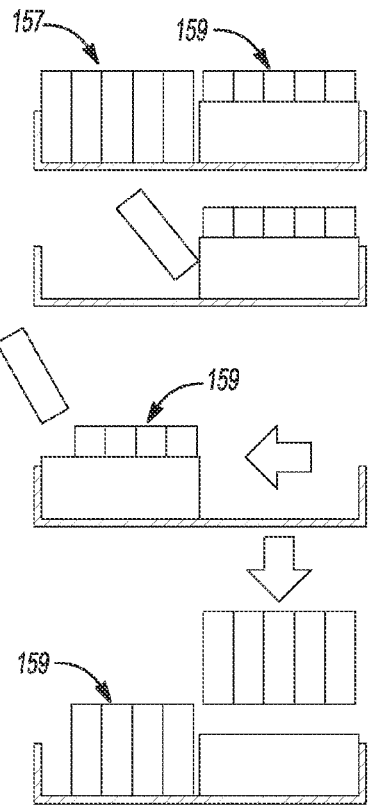
Figure 17C:
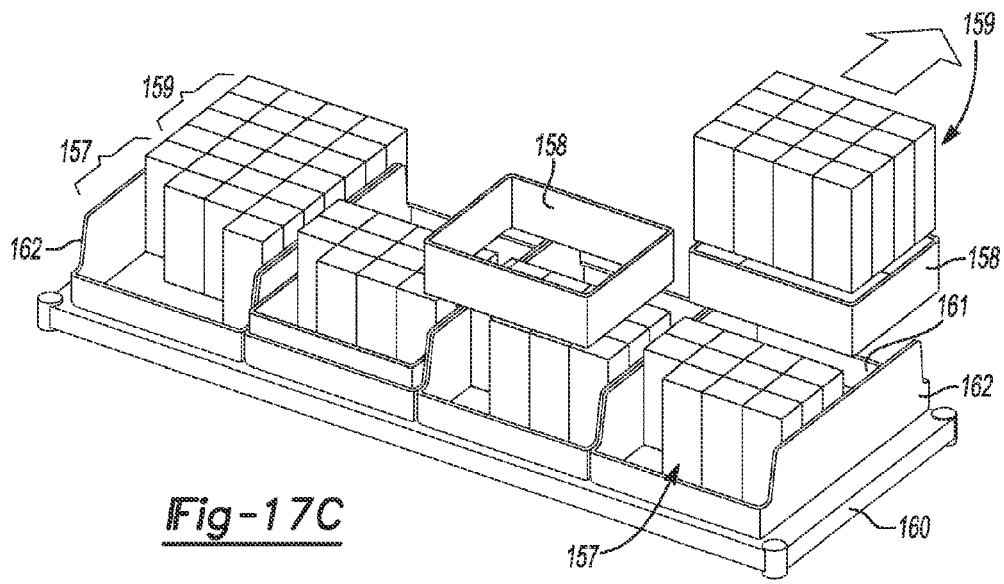
Figure 18A:
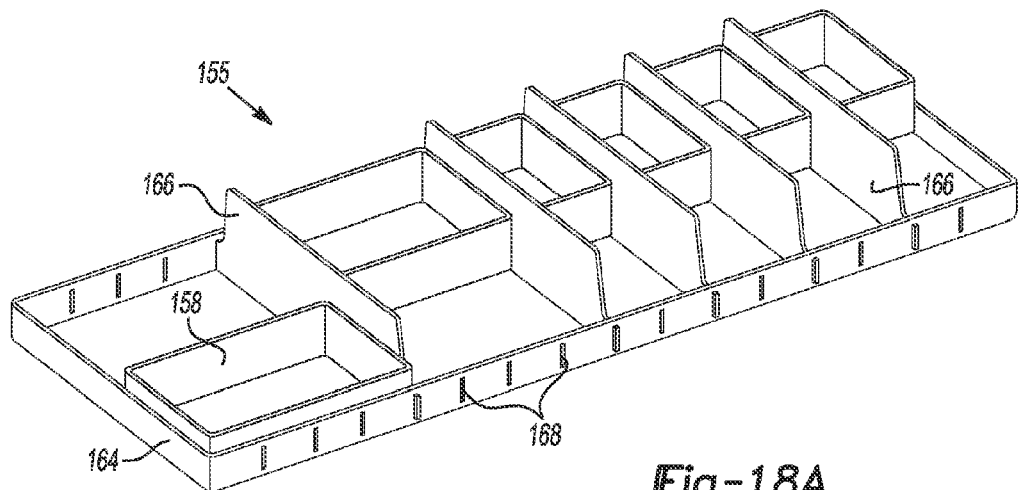
Figure 18B:
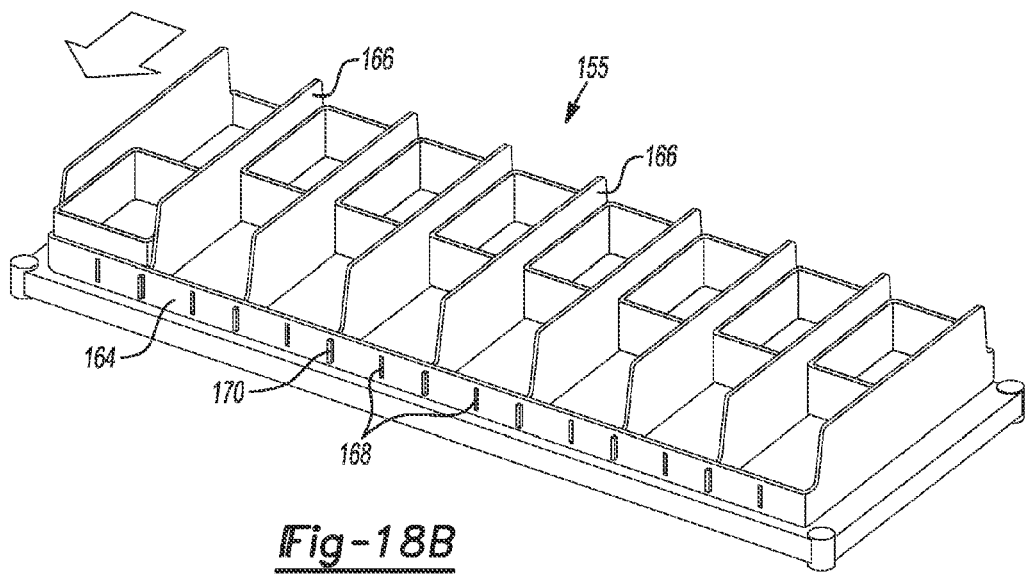
Figure 20A:
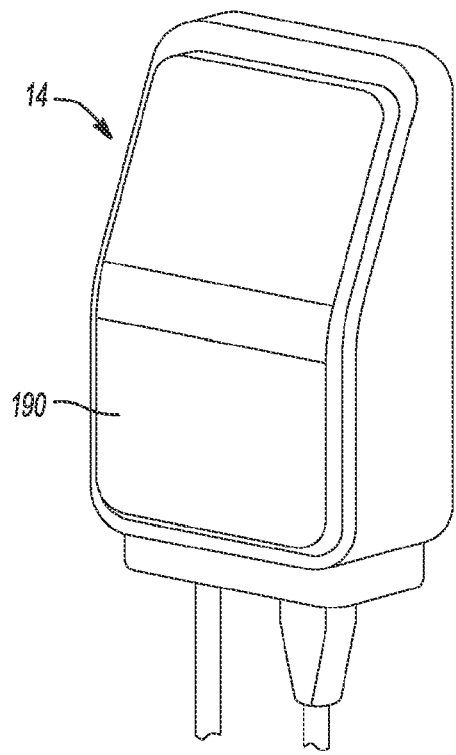
Figure 20B:
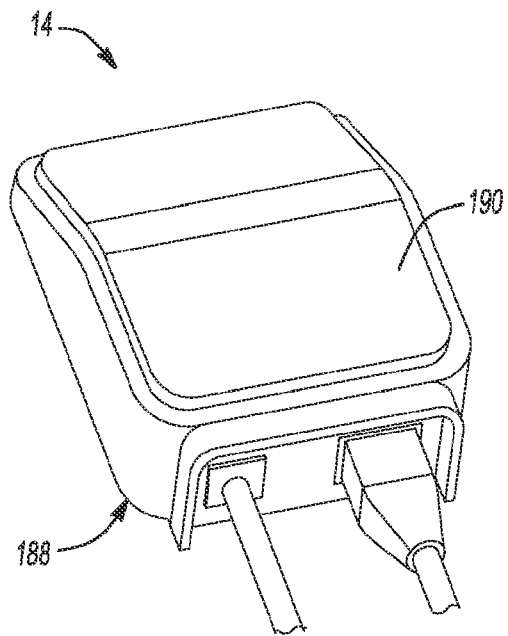
Figure 21:
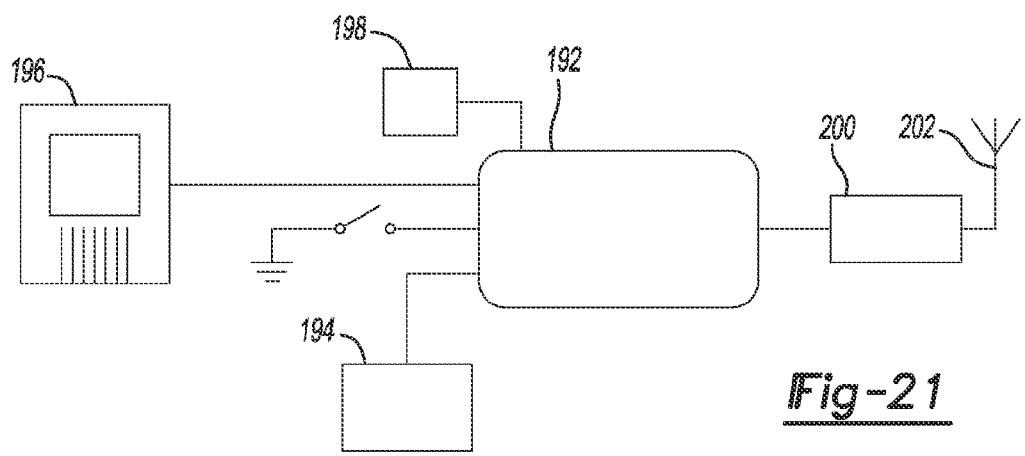
Figure 22:
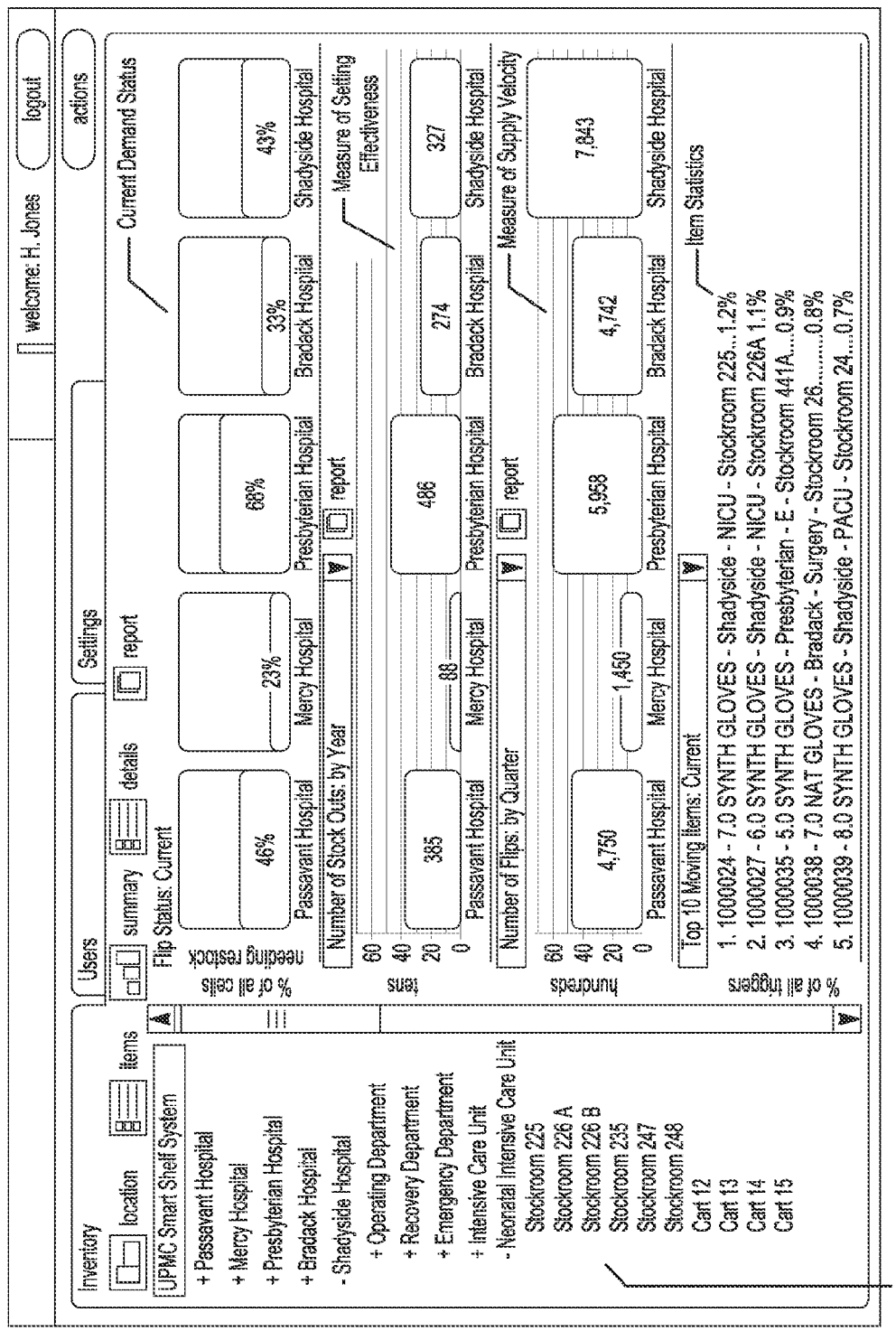
Figure 23:
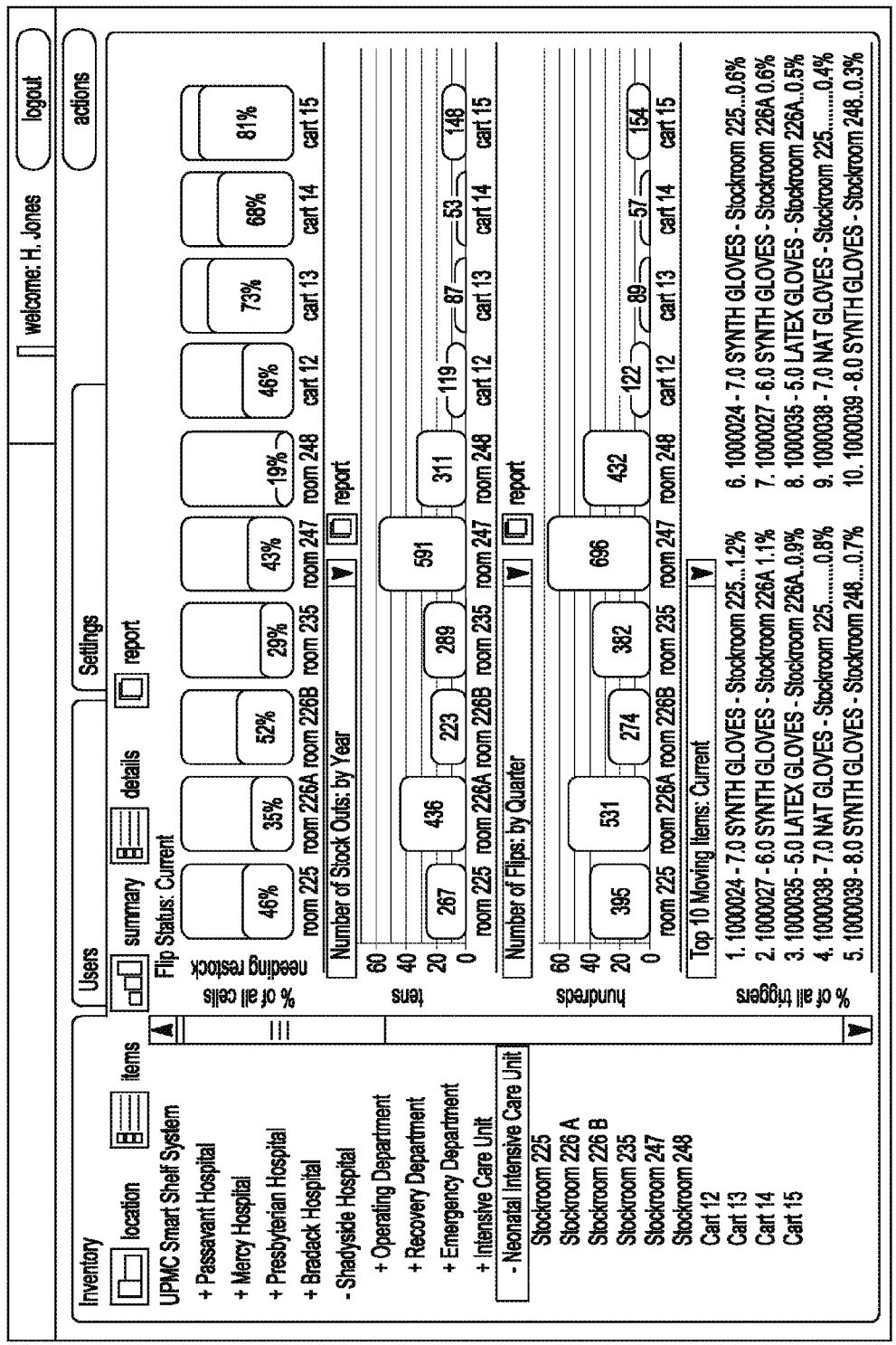
Figure 30A:
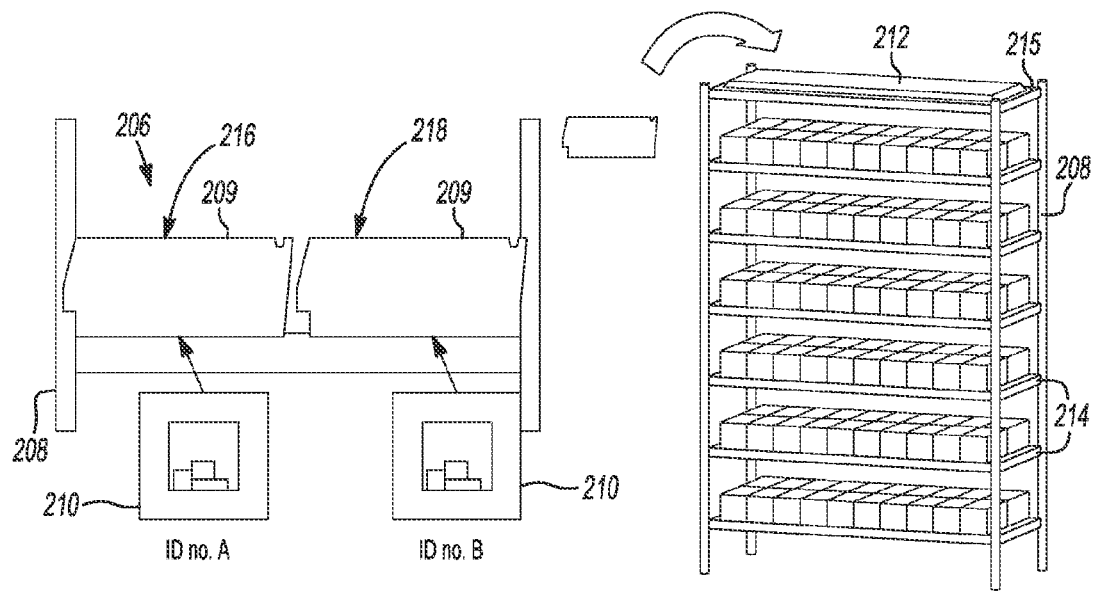
Figure 30B:
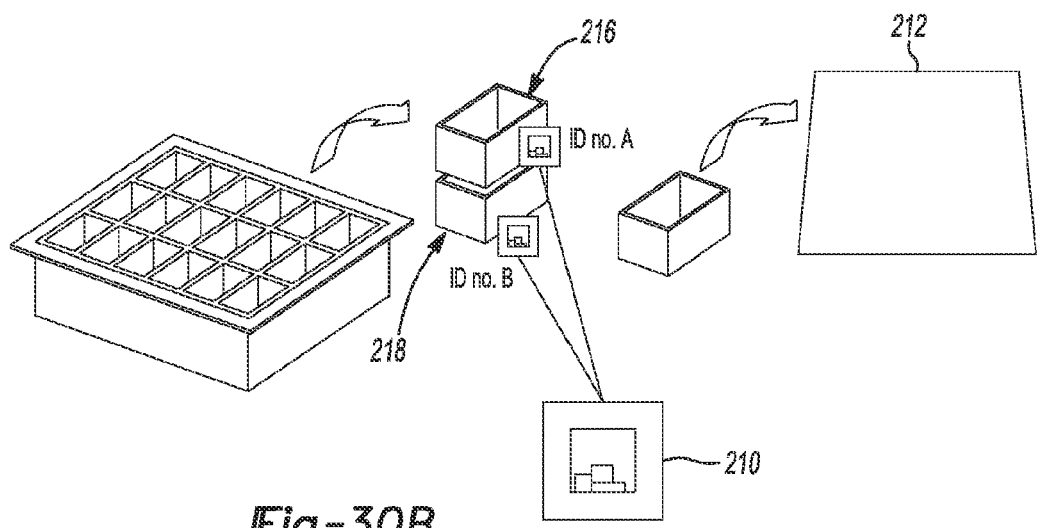
Figure 31A:
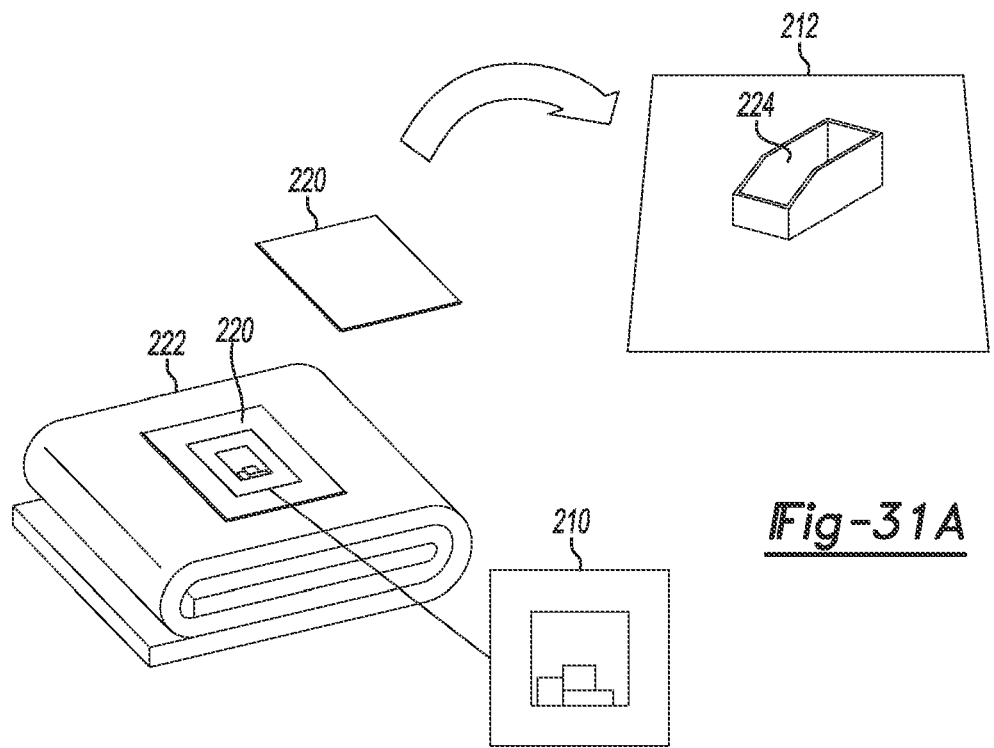
Figure 31B:
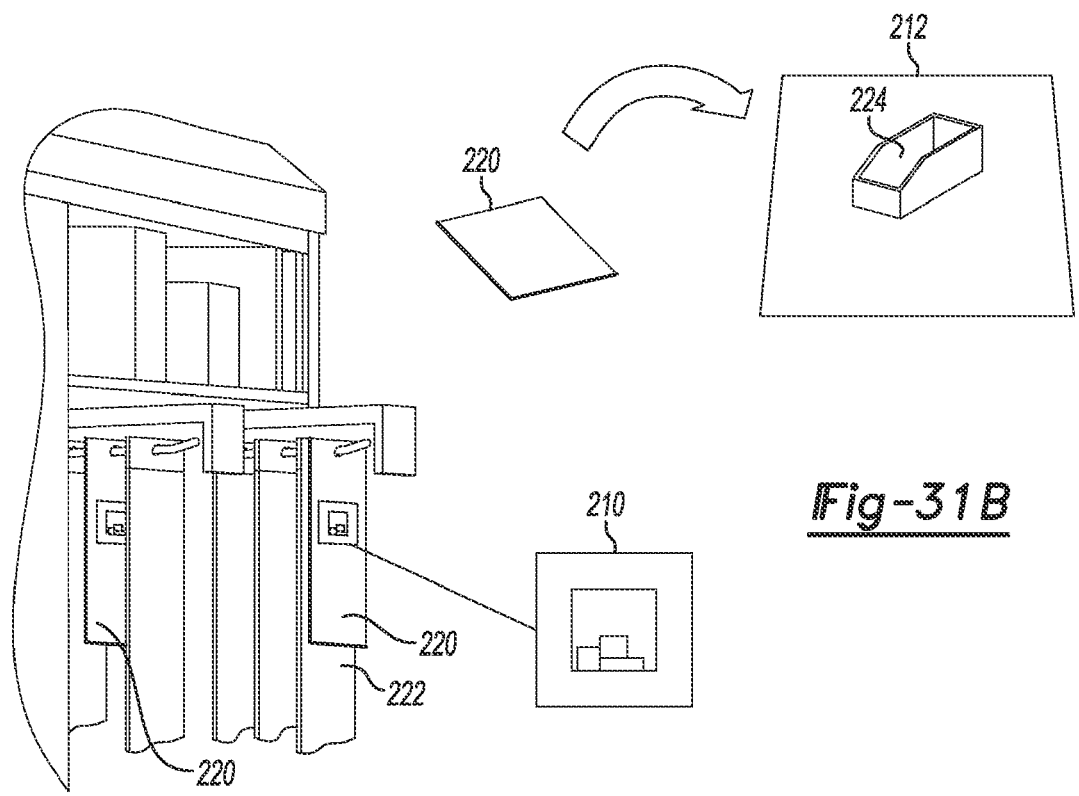

FIG. 17A shows yet another exemplary embodiment of an inventory storage module for the inventory management system of the present disclosure;

FIGS. 17B and 17C illustrate an exemplary protocol for using the inventory storage module of FIG. 17A according to the inventory management system of the present disclosure;

FIGS. 18A and 18B show additional exemplary embodiments of inventory storage modules for the inventory management system of the present disclosure;

FIG. 19A shows another exemplary embodiment of an inventory storage module for the inventory management system of the present disclosure;

FIG. 19B illustrates an exemplary protocol for using the inventory storage module of FIG. 19A according to the inventory management system of the present disclosure;

FIGS. 20A and 20B depict an exemplary data reader module for the inventory management system of the present disclosure;

FIG. 21 is a schematic block diagram of the data reader module for the inventory management system of the present disclosure;

FIGS. 22-29 relate to and show various aspects of an exemplary inventory data management module the inventory management system of the present disclosure;

FIGS. 30A and 30B illustrate still additional exemplary embodiments of inventory storage modules for the inventory management system of the present disclosure; and FIGS. 31A and 31B show further exemplary embodiments of an inventory management system of the present disclosure.

Corresponding reference numerals indicate corresponding parts throughout the several views of the drawings.

DETAILED DESCRIPTION

Example embodiments of the inventory management system of the present disclosure will now be described more fully with reference to the accompanying drawings. These example embodiments are provided so that this disclosure will be thorough, and will fully convey the scope to those who are skilled in the art. Numerous specific details are set forth such as with examples of specific components, devices, and methods, are intended to provide a thorough understanding of embodiments of the present disclosure. It will be apparent to those skilled in the art, however, that specific details need not be employed, that example embodiments may be embodied in many different forms and that neither should be construed to limit the scope of the disclosure. In some example embodiments, well-known processes, well-known device structures, and well-known technologies are not described in detail.

Figure 1:
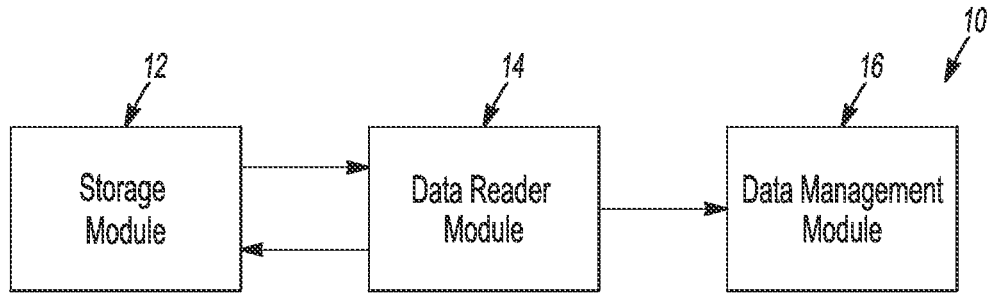
FIG. 1 is a schematic block diagram illustrating an inventory management system according to the present disclosure.
Figure 2:
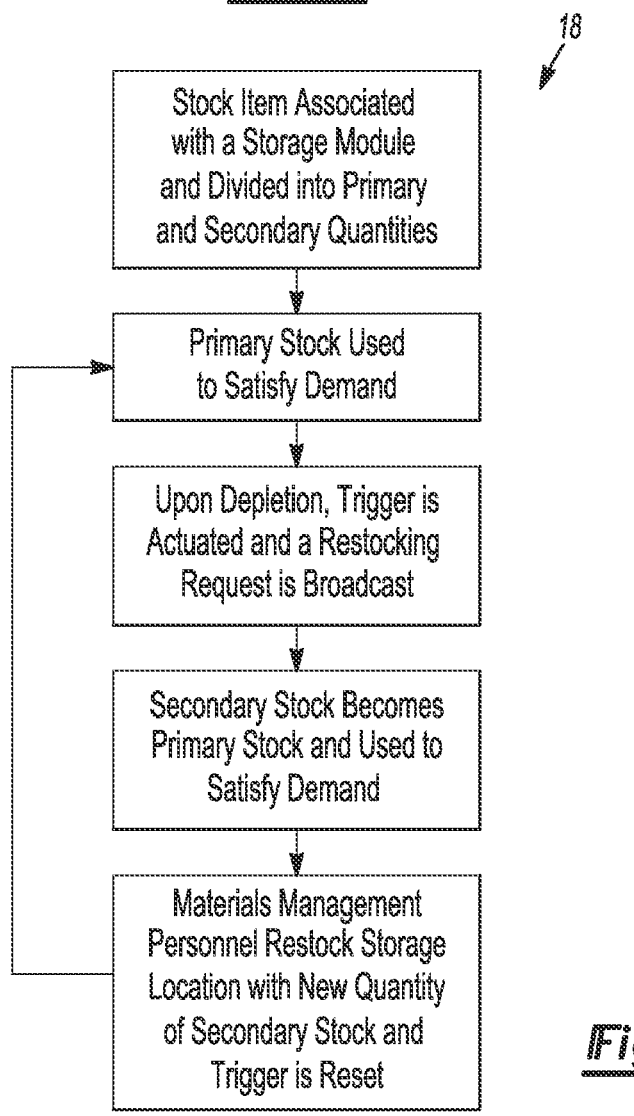
FIG. 2 is a schematic block diagram showing an exemplary protocol for the inventory management system of the present disclosure.

With overall reference to the figures, and particularly to FIGS. 1 and 2, the inventory management system 10 of the present disclosure can generally include an inventory storage module 12, a data reader module 14, and an inventory data management module 16 that cooperate and interact generally according to an inventory management protocol 18 for the inventory management system.

In general, several inventory management system solutions are provided in the present disclosure and operate according to a similar protocol. A storage module 12 contains a predetermined total quantity of a stock item that is made available to users from the inventory of a storage location in a managed operation. A unique identifier for the storage module 12 is synchronized to, and recognized in, an inventory data management module 16. Detailed information about the storage module 12 and the stock item are associated in the data management module 16. The storage module and data management module are intermediately coupled or networked to a data reader module according to well-known communication protocols. The data reader module is typically located remotely from both the storage module and the data management module. Alternatively, and depending upon the configuration, size or other features of a particular managed operation, the functionality of the data reader module may be encompassed within the capabilities of the data management module, and a separate data reader module may be omitted. The predetermined total quantity of the stock item is subdivided into a first (e.g., primary) quantity and a second (e.g., secondary) quantity, with the first quantity being located at a readily accessible (e.g., a front) first section of the storage module and the second quantity being located at a generally less accessible (e.g., rear) second section of the storage module. Regular user demands for the stock item, such as during the normal workflow at the storage location, are satisfied by items from the first (primary) quantity. When the first (primary) quantity of the stock item is depleted from the storage module, necessitating the user to access the second (secondary) quantity in order to satisfy demand for the item, a trigger on the storage module is activated to initiate a request to restock the storage module, placing the storage module in a restocking condition.

In an exemplary embodiment of the present disclosure, the storage module broadcasts a radio frequency signal representing the storage module's restocking request. Demand for the stock item in the continued normal workflow of the managed operation is subsequently satisfied from the secondary quantity of the stock items still remaining in the storage module, which can be moved from the second section to the first section of the storage module to thereby become the primary quantity of stock. The restocking request signal is received and/or recorded at the data reader module, and is subsequently rebroadcast, retransmitted, or otherwise redirected by the data reader module to the data management module. The restocking request signal is received at the data management module. Upon receipt of the restocking request, materials management personnel administering the inventory management system are tasked to resupply the storage module with the stock item. At the same time, detailed information concerning item usage at the particular storage location is recorded in the data management module. As such, the inventory management system enables detailed, real-time inventory tracking and analysis to performance criteria that may be defined, for example, by administrators of the managed operation. As part of the restocking activity, materials management personnel reset the trigger on the storage module, thereby placing the storage module in a reset condition and resetting that storage location within the inventory management system. The (primary) stock items remaining in the storage module are kept at the first portion of the storage module. The resupplied (secondary) stock items are then located at the rear section of the storage module. The protocol is thereby readily repeatable.

It should be understood that the protocol for the inventory management system of the present disclosure promotes a "first in, first out" consumption of stock. In this manner, waste and stock loss due to expiry are minimized. Moreover, since the same fixed quantity of an item may be supplied in each restocking event, restocking operations are simplified as compared with PAR systems.

Several inventory storage modules that are suitable for use in the inventory management system 10 of the present disclosure are shown in the figures. Referring to FIGS. 3, 4A, and 4B, one exemplary inventory storage module 20 comprises a storage bin 22 and a nested sleeve 24. The sleeve 24 is received within the interior space 26 of the storage bin 22. The sleeve 24 is sized to selected dimensions of the interior of the storage bin 22, such as by approximating the width (W) dimension(s) of the storage bin 22 as shown in the exemplary embodiment in FIGS. 3, 4A and 4B. Another dimension (L) of the sleeve 24 varies relatively significantly from a corresponding dimension of the storage bin 22. For example, in the exemplary embodiment, the overall length (L) of the sleeve 24 is about half of the length of the interior space of the storage bin 22. Consequently, the sleeve 24 is moveable within the interior space 26 of the storage bin 22. In the arrangement shown, the sleeve 24 is moveable between front 28 and rear 30 sections of the storage bin 22 without having to remove the sleeve 24 from the interior space 26 of the storage bin 22. For example, the sleeve 24 is slidable inside of the storage bin 22. Of course, depending upon the configuration of the storage bin 22, the sleeve 24 can be modified to accommodate any of a variety of storage volumes or interior dimensions.

As shown in FIGS. 3, 4A and 4B, a front section of the sleeve 24 comprises a control portion 32 and a rear section of the sleeve 24 comprises a containment portion 34. The containment portion 34 generally defines a perimeter of an interior volume within the storage bin 22 which, in the exemplary embodiment shown in the figures, occupies about one-half of the interior volume of the storage bin 22. One embodiment of a containment portion 34 is best shown in FIG. 3 and comprises a rectangular, wall-like perimeter structure that has no bottom enclosure. Of course, the containment portion 34 may take the form or comprise structure having any other suitable geometric configuration, depending on the size and shape of the corresponding storage bin 22 in which it may be used. In use, the containment portion 34 of the sleeve 24 captures the second quantity of stock items within the storage bin 22, which may be half or about half of the predetermined quantity of stock items that are desired to be available on-hand. In this regard, the containment portion 34 segregates the second quantity of stock items from the first quantity of stock items in the storage bin 22.

The control portion 32 of the sleeve 24 is attached to the front of the containment portion 34. The control portion 32 generally includes a trigger device 36, such as a "flag" or the like, that is movably attached at an upper end of a body structure 38. The body structure 38, in turn, houses a computer module 40, such as a microprocessor, for example, a sensor unit 42, and a battery/power supply 43 (see FIG. 12).

The computer module 40 can comprise a programmable or programmed device and memory 44, and maintains an identification code that uniquely identifies the particular storage module 20 to the inventory management system 10. The computer module 40 may comprise and/or be coupled to a transceiver 46 and an antenna 48 that are operable to generate, receive and/or broadcast a radio frequency (RF) signal containing the storage module's 20 identification code and/or other specific information about the identity and/or condition of the storage module 20 and/or the stock items contained therein. Any of a variety of readily available, off-the-shelf microprocessors, such as may be purchase from Texas Instruments, are suitable for use in the computer module 40 of the disclosure.

Figure 28:
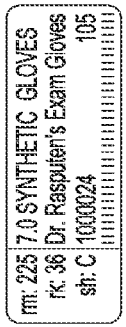
Figure 29:

As shown, for example, in FIG. 28, when a stock item is included within the inventory management system 10, a variety of data are associated with the storage module 12 by the data management module 16. In this respect, each of the hundreds or thousands of individual storage modules 12 that may be associated with the inventory management system 10 throughout the managed environment is individually identified and synchronized to the data management module 16.

The sensor unit 44 of the storage module 20 is operable to detect the movement and/or position of the trigger device 36, for example, relative to the body structure 38. A suitable device for the sensor unit 44 includes a Hall effect sensor. When the sensor unit 44 detects operation of the trigger device 36, the computer module 40 generates and broadcasts the radio frequency signal that represents a restocking request by a user of the system 10.

Referring to the exemplary embodiment of FIGS. 4A and 4B, the trigger device 36 can take the form of a "flag" that pivots between a raised position (FIG. 4A) and a lowered position (FIG. 4B) as controlled by a manual input from a user. When the "flag" is in the raised position, as shown in FIG. 4A, the storage module 20 is in an initial or reset condition. In this condition, the storage module 20 contains the first and second quantities of stock items and the sleeve 24 is located at a rear section 30 of the storage bin 22. As generally described above, when the first quantity of stock items has been depleted from the storage bin 22, the user actuates the trigger device 36 thereby initiating the restocking request. In this regard, the user can use the "flag" as a handle with which to grasp the sleeve 24 in order to slide it from the rear section 30 of the storage bin 22 to the front section 28 of the storage bin 22. As the sleeve 24 moves to the front section 28 of the storage bin 22, the second quantity of stock items is brought with it. After the storage module 20 and stock items are positioned at the front section 28 of the storage bin 22, the "flag" can be rotated toward the front the storage bin 22 to the lowered position, where it can come to rest against a front ledge 50 of the storage bin 22 as shown in FIG. 4B. The movement of the "flag" toward the lowered position is sensed by the sensor unit 44, which causes the computer module 40 to broadcast the request to restock the storage bin 22.

As shown in FIGS. 4A and 4B, the storage bin 22 includes an identification label 52, such as the label disposed on its front ledge 50 in FIG. 4A. A corresponding identical identification label 54 is located on a front surface of the control portion 32. The labels 52, 54 are created in the data management module 16 when the storage module 20 and/or stock item is synchronized and/or entered into the system 10 as discussed further below. When the trigger device 36 "flag" is placed in the lowered position, it covers the label 52 on the storage bin, so that only the label 54 on the control portion 32 is visible to a user.

Additional features of the control portion 32 can include an LED 56 or other indicia that can visually indicate a status condition of the storage module 20, such as being in one of the reset or restocking conditions. Other status indicators, such as visible or audible indicators, may also be employed.

The storage bins 22, body structures 38 and trigger devices 36 of the control portions 32, and the containment portions 34, can be manufactured from any of a variety of suitable materials providing for their economical manufacture and durability, including many kinds of plastics and lightweight metals.

With additional reference to FIG. 2, an embodiment of the inventory management system 10 of the present disclosure can operate according to the following exemplary protocol:

A stock item is added to the inventory management system and associated with a specific location in the managed environment.

Identical storage bin and sleeve labels are generated and affixed to the storage bin and its associated sleeve of an inventory storage module.

The sleeve is placed in a rear section of its associated storage bin.

The stock item is placed in the inventory storage module, divided into two equal quantities: a first quantity of the item is located in the front section of the storage bin; and a second quantity of the item is located in the rear section of the storage bin and within the confines of the containment portion of the sleeve.

The restocking trigger or "flag" is placed in a raised position placing the storage module in an initial condition.

Upon demand for a stock item, a user depletes the first quantity of items from the front section of the storage bin.

When demand results in the user retrieving the last item from the first quantity of items (or in a subsequent user retrieving the first item from the second quantity of items), the user moves the sleeve (together with the second quantity of stock items) from the back section of the storage bin to the front section of the storage bin (e.g., by sliding it within the storage bin).

The user moves the "flag" to a deployed position by rotating the flag toward a position over the front ledge of the storage bin.

The storage module broadcasts a RF signal indicative of a restocking request.

The restocking request signal is received at a data reader module and transmitted by the data reader to the data management module.

The restocking request signal is received and interpreted at the data management module.

Materials management personnel are notified of the restocking request.

Metrics relating to the stock item and storage module are recorded in the data management module.

During restocking of the storage bin by materials management personnel, the sleeve is removed from the front section of the storage bin (e.g., it is lifted out) while maintaining the remaining portion of the second quantity of the stock item at the front section of the storage bin (e.g., aided by the fact that the containment portion of the sleeve has no bottom). The sleeve is replaced at the back section of the storage bin and a first quantity of the stock item is placed within the confines of the sleeve's containment portion.

The "flag" is placed in the raised position and the storage module is reset to a reset condition.

The protocol is repeated as required.

Additionally, the inventory storage module 12 can comprise various storage configurations. As best seen in FIG. 5, a variety of storage bin sizes and types are contemplated within the present disclosure, and various shapes can also be employed. The present system 10 and its components therefore offer considerable flexibility and provide a host of storage solutions for many different configurations using alternative shelving devices, and the like.

Alternative embodiments of an inventory storage module are illustrated in FIG. 5. In these alternative configurations, the storage modules 58, 60 do not include a storage bin, as previously described. Instead, the storage modules 58, 60 are associated directly with individual shelves 62 of a storage rack device 64, or the like. This form of storage module 58, 60 is particularly well-suited for association with inventory stock items that are too large or bulky to be contained in storage bins. The storage module 58, 60 of this type includes only a control portion 66 as generally described in the prior discussion. The trigger device 68 for this storage module is much larger than the other and serves a dual function. In addition to initiating the events resulting in a restocking request, the much larger "flag" of the alternate storage module 58, 60 serves as a barrier or divider to shield the second quantity of stock items, providing a visual indicator to the user as to the order in which the shelved stock items should be depleted.

To describe one example of the alternate storage module 58 in better detail, reference is made to FIG. 5. In FIG. 5, large stock items 70 are contained on shelves 62 of a conventional rack device 64, shelving unit or other storage device. The storage module 58 is attached directly to the shelf 62 containing its associated stock items 70. The "flag" of the trigger device 68 is a panel that is pivotally attached to the body structure 72 of the control portion 66. The pivot axis X1 of the "flag" extends vertically upward and generally orthogonal to the shelf 62. Thereby, a face of the "flag" is operable to obscure a portion (e.g., the second quantity) of the stock items 70 contained on the shelf. Configured in this manner, the storage module 58 provides a visual indicator to a user that directs the user to the stock items 70 that should be removed from the shelf to satisfy a demand for the item. When the first quantity of stock items 70 is depleted, the user rotates the "flag" 68 about the vertical pivot axis X1 about 180 degrees from its prior position to provide easy access the second quantity of items. This can be commonly understood as a "side-to-side"-type storage module. Moving the "flag," of course, initiates the restocking request as already described.

Another example of an alternate storage module 60 is also shown in FIG. 5. The principle for this further alternative is the same as just described, however the "flag" is configured to move between positions so as to obscure one of two quantities of stock items located on one of two adjacent shelves of a conventional shelving unit, instead of one of two quantities of stock items located adjacently on a single shelf. In this respect, the pivot axis Y1 of the "flag" extends horizontally and generally parallel to the shelf. As such, a face of the "flag" is operable to obscure the portion of the stock items contained on one of the adjacent shelves. This type of storage module can be commonly understood as an "over/under"-type storage module.

Additional embodiments of storage modules for the inventory management system according to the disclosure can be understood with reference to FIGS. 6-16. As shown in FIGS. 6-12, the storage module 74 of the inventory management system 10 includes a storage bin 76 and a divider member 78 received within the interior space 80 of the storage bin 76. The divider member 78 generally separates the interior volume 80 of the storage bin 76 into two sections, such as a more readily accessible front, first section 82 and less accessible rear, second section 84. The divider member 78 generally includes a base portion 86 and a partition portion 88.

Figure 12:
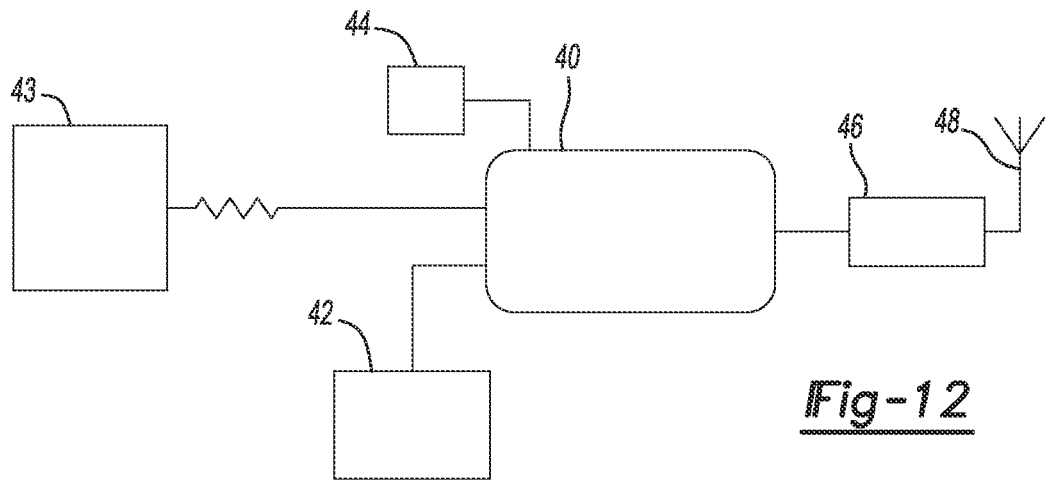
FIG. 12 is a schematic block diagram of a computer module.

The base portion 86 comprises a very low power, battery operated device that can broadcast a restocking request when the inventory level of its associated storage bin 76 is low. Referring particularly to FIGS. 9, 11 and 12, the base portion 86 comprises a body structure 90 including a base cover 92 and a base plate 93. The base portion 86 of the divider member 78 can be securely attached to a surface of the storage bin 76, such as by standard fastening devices and methods, adhesives, and the like, so that its position within the storage bin 76 is fixed. The body structure 90 houses a computer module 40, such as a microprocessor, a sensor unit 42, and a battery/power supply 43. As discussed previously, the computer module 40 can comprise a programmable or programmed device having memory 44, and maintains an identification code that uniquely identifies the particular storage module to the inventory management system 10. In addition, the computer module 40 may comprise and/or be coupled to a transceiver 46 and antenna 48 that are operable to generate, receive and/or broadcast a radio frequency (RF) signal, including a RF signal containing the storage module's identification code and/or other information about the identity and/or condition of the storage module and/or the stock items contained therein.

The partition portion 88 of the divider member 78 serves as a quasi wall-like structure that promotes the separation of the two sections 82, 84 of the interior space 80 of the storage bin 76. As shown in FIGS. 9 and 10, for example, the partition portion 88 can include a panel 93 and a pedestal 94. The panel 93 can take any of a variety of forms, such as a generally rectangular panel, and can be appropriately dimensioned to accommodate various sized storage bins 76. Optionally, the panel 93 can include slots or apertures 96 that enable a user to see through the panel 93, or the panel 93 can be transparent. In use, the partition portion 88 is adapted to be received on top of the base portion 86 and it is readily visible in the storage bin to a user of the system, as illustrated in FIG. 6. In this regard, the pedestal 94 is received in a receptacle 98 of the base portion 86. In addition, as best seen in FIG. 9, a magnet 100 is included in the pedestal 94 and cooperates with a metal catch member 102 housed in the receptacle 98 to help attach the partition portion 88 to the base portion 86.

The sensor unit 42 of the storage module 74 is operable to detect the movement and/or position of the partition portion 88 relative to the base portion 86. In this respect, the partition portion 88 serves as a trigger device for the storage module 74. The trigger function of the partition portion 88 is initiated by a user removing or dislodging the partition portion 88 from the base portion 86, such as shown in FIGS. 7B and 9. For example, in a well-known manner, a Hall Effect sensor is operable to detect a change of state in a magnetic field that occurs when the magnet 100 in the partition portion 88 is separated or disassociated from the metal catch member 102 in the base portion. As previously described, when the sensor unit 42 detects operation of the trigger device, the computer module 40 generates and broadcasts the radio frequency signal that represents a restocking request by a user of the system 10.

Figure 7A:
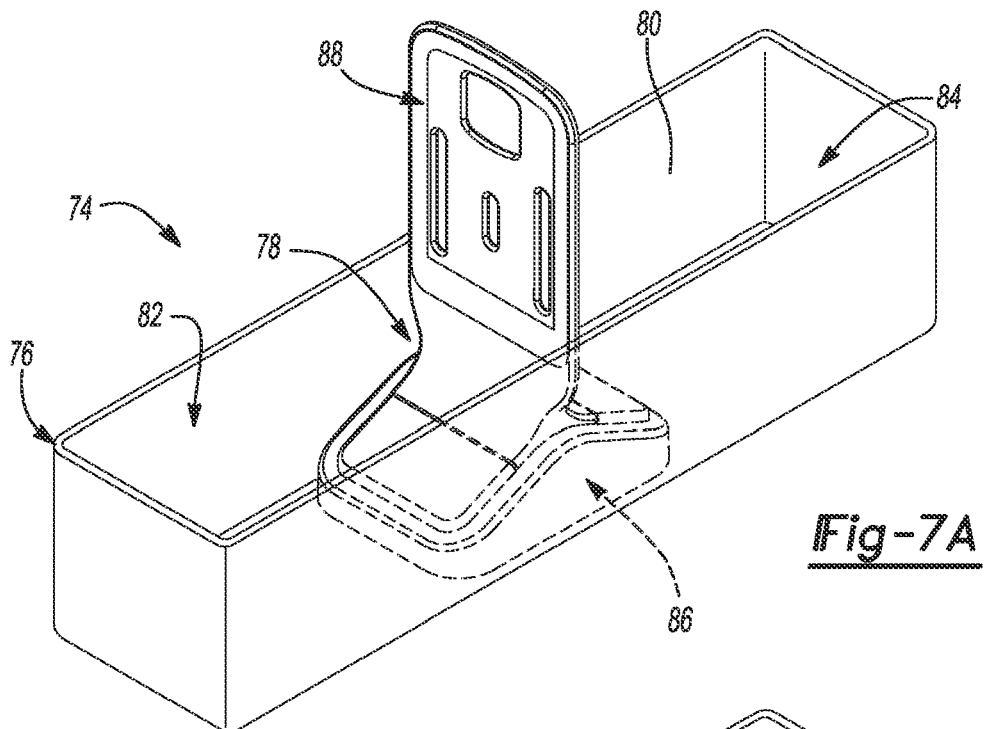
FIG. 7A shows the inventory storage module of FIG. 6 in an initial or reset condition.
Figure 7B:
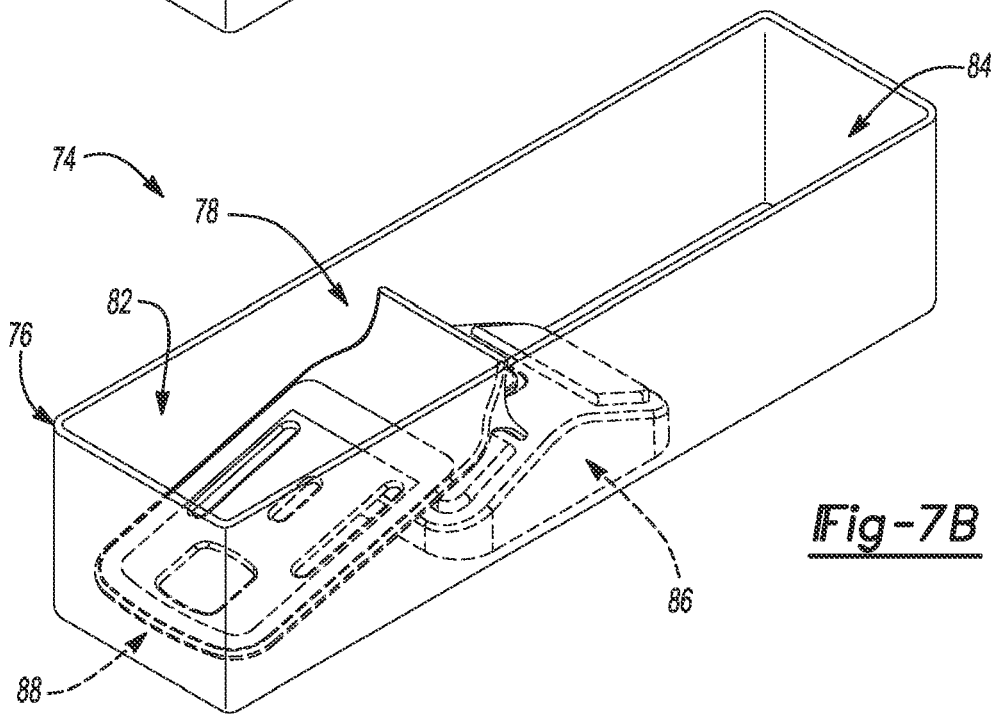
FIG. 7B shows the inventory storage module of FIG. 6 in a triggered, restocking condition.

With reference to FIGS. 7A and 8, when the partition portion 88 is positioned on the base portion 86, the storage module 74 is in the initial or reset condition. In this condition, the storage module 74 is stocked with the first quantity of stock items located at a front section 82 of the storage bin 76 and second quantity of stock items located at a rear section 84 of the storage bin 76. As generally described above, when the first quantity of stock items has been depleted from the storage bin 76, the user actuates the trigger device 88 thereby initiating the restocking request. In this regard, the user can completely remove the partition portion 88 from the base portion 86 or, alternatively, tip over the partition portion 88 to a lowered position (see FIGS. 7B and 9), such that the magnet 100 is separated or disassociated from the metal catch member 102 on the base portion 86. In doing so, the removal or other movement of the partition portion is detected by the sensing unit 42, and a request to restock the storage bin is subsequently generated and broadcast by the computer module 40.

Figure 13:
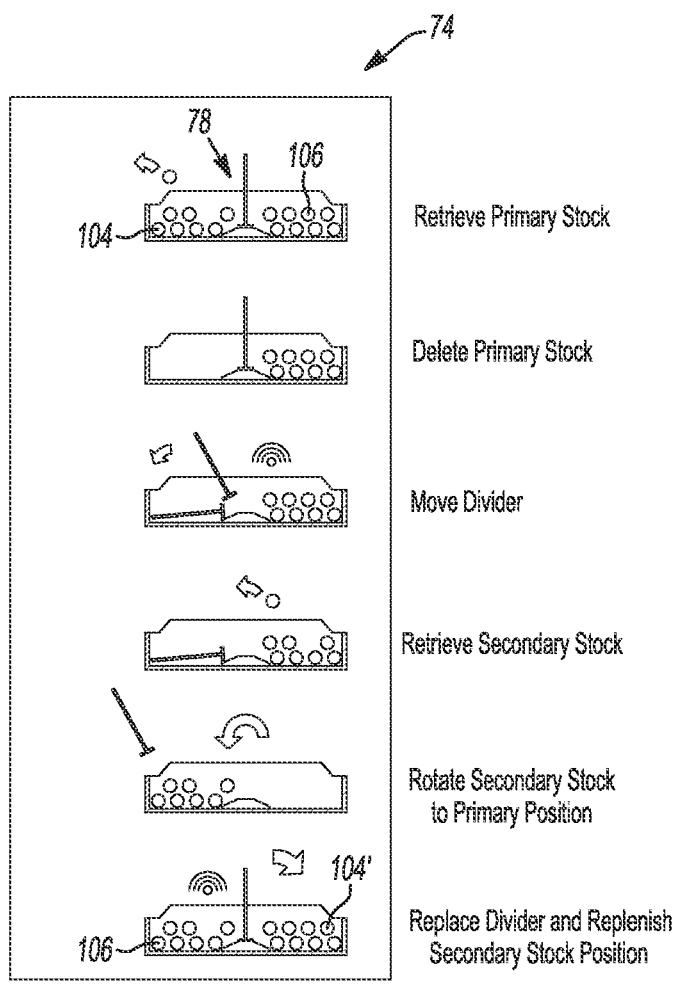
FIG. 13 illustrates an exemplary protocol for using the inventory storage module of FIG. 6 according to the inventory management system of the present disclosure.

With continued reference to FIGS. 7A, 7B and 13, an inventory management system can operate according to the following exemplary protocol:

- A stock item is added to the inventory management system and associated with a specific location in the managed environment.
- Storage bin and partition portion labels are generated and affixed to the storage bin and its associated divider member 78 of an inventory storage module.
- A divider member 78 is secured in its associated storage bin 76.
- The stock item is placed in the inventory storage module 74, divided into two equal quantities: a first quantity 104 of the item is located in the front section 82 of the storage bin 76; and a second quantity 106 of the item is located in the rear section 84 of the storage bin 76, the divider member 78 separating the front section 82 of the storage bin 76 from the rear section 84 of the storage bin 76 and the first quantity of the stock item 104 from the second quantity 106 of the stock item.
- The partition portion 88 is placed on the base portion 86 of the divider member 78, placing the storage module 74 in an initial condition.
- Upon demand for a stock item, a user depletes the first quantity 104 of items from the front section 82 of the storage bin 76.
- When demand results in the user retrieving the last item from the first quantity 104 of items (or in a subsequent user retrieving the first item from the second quantity 106 of items), the user removes or tips over the partition portion 88 placing the divider member 78 in a restocking condition.
- The computer module 40 broadcasts a RF signal indicative of a restocking request.
- The restocking request signal is received at a data reader module 14 and transmitted by the data reader module 14 to the data management module 16.
- The restocking request signal is received and interpreted at the data management module 16.
- Materials management personnel are notified of the restocking request.
- Metrics relating to the stock item 104 and storage module 74 are analyzed and/or recorded in the data management module 16.
- During restocking of the storage bin 76 by materials management personnel, the second quantity of stock items 106 is moved from the back section 84 of the storage bin 76 to the front section 82 of the storage bin 76 and a "new" first quantity 104' of the stock item is placed at the back section 84 of the storage bin 76.
- The partition portion 88 is returned to its initial position on the base portion 86 of the divider member 78, placing the storage module in a reset condition (e.g., either before or after restocking occurs).
- The protocol is repeated as required.

Figure 14A:
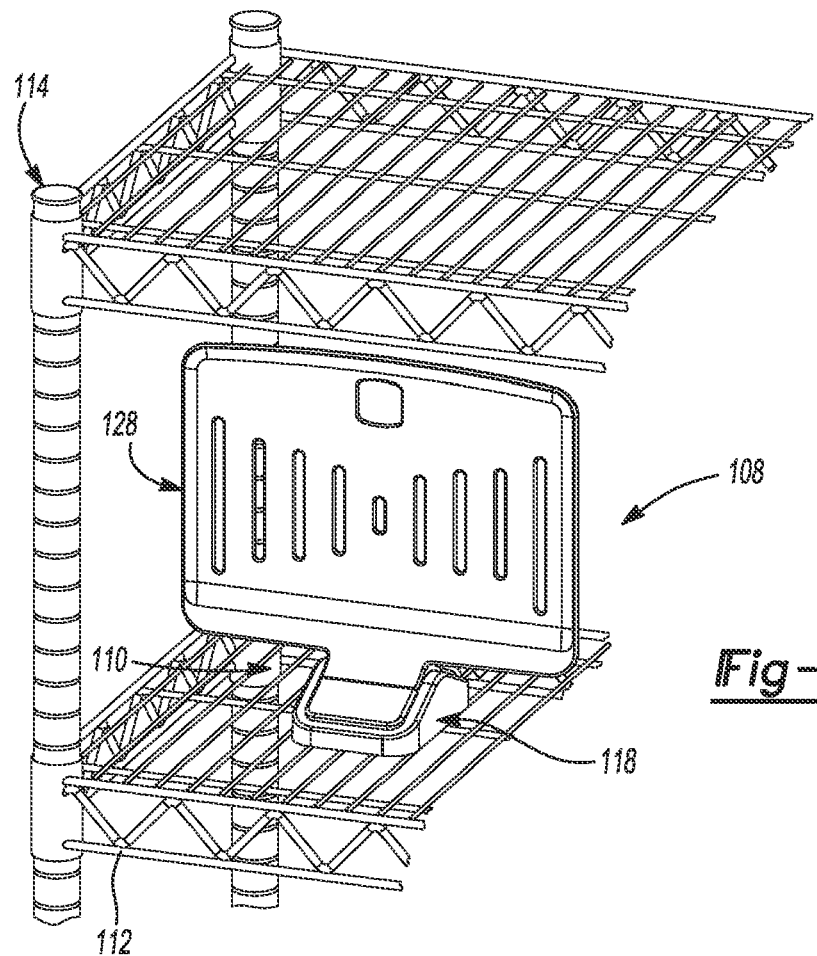
FIG. 14A and FIG. 14B show an alternative exemplary embodiment of the divider member adapted for use with a storage shelf.
Figure 14B:
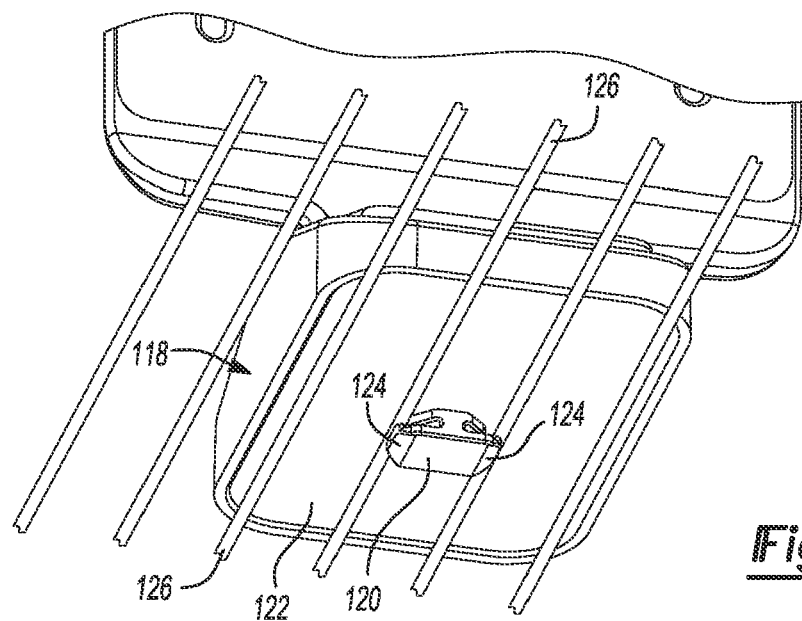

An alternative to the inventory storage module of FIG. 6 is shown in FIGS. 14A and 14B. This configuration of a storage module 108 does not include a storage bin, as previously described, and is comparable to the storage module configurations 58, 60 of FIG. 5. This form of storage module 108 is particularly well-suited for association with inventory stock items that are too large or bulky to be contained in storage bins. The storage module 108 of this type includes only a divider member 110 as generally described above. The divider member 110 is associated directly with individual shelves 112 of a storage rack device 114, or the like.

In addition, as seen in FIG. 14B, the body structure 116 of the base portion 118 can include a cleat or anchor 120 included at the underside of the base plate 122 that enables the base portion 118 of the divider member 110 to be securely affixed to the shelf 112 on which it is located. The cleat 120 includes hook portions 124 that can engage, for example, the shelving bars 126 of a storage rack 114 in an installed condition. To attach the base portion 118 to the shelf 112, then, the cleat 120 is oriented to allow the hook portions 124 to pass through the shelving bars 126. Thereafter, the base portion 118 is rotated such that the hook portions 124 engage the shelving bars 126 to secure the base portion 118 in place on the shelf 112.

The partition portion 128 serves as the trigger device for this storage module 108 as already described. The size of the partition portion 128 can vary with the size of the stock items to be associated with the storage module 108 and will generally tend to be larger than the partition portions sized for operating within a storage bin. In addition to initiating the events resulting in a restocking request when triggered, the much larger partition portion also serves as a barrier or divider to shield the second quantity of stock items, providing a visual indicator to the user as to the order in which the shelved stock items should be depleted, as previously described.

One example of the alternate storage module can be described as follows. Large stock items are contained on a shelf of a conventional rack device or shelving unit. The storage module is attached directly to the shelf containing its associated stock items. The partition portion is placed on the base portion. Configured in this manner, the storage module provides a visual indicator to a user that directs the user to the stock items that should be removed from the shelf to satisfy a demand for the item. When the first quantity of stock items is depleted, the user removes or tips over the partition portion. The partition portion is separated or disassociated from the base portion, triggering a restocking request and providing access to the second quantity of stock items in a manner similar to that already described.

It can also be appreciated that the partition portion may take a variety of alternate forms, such as shown in FIGS. 16A, 16B and 16C, to accommodate stock items not easily situated in a storage bin or on the shelf of a storage rack. For example, a partition portion 130 can comprise a plurality of panel members 132 oriented or positioned in a plurality of planes (see FIG. 16C). The panel member(s) can also be jointed and/or pivotable relative to one another in order to better conform to the stock items. Further, the panel member(s) 132 can be integral or separable from the pedestal 134 of the partition portion, as shown in FIG. 16B. As yet another alternative, a partition portion 136 can comprise a flexible strap or band. With particular reference to FIG. 16A, a flexible strap 138 is attached to the pedestal 140 at one end and includes an attachment bracket 142 at the opposite end. The attachment bracket 142 can be operable to be secured to a shelf, bin or other platform with which the storage module is associated.

Yet another alternate configuration of a divider member and partition portion 144 is shown in FIG. 15. This partition portion 144 can be suitable for applications where the size, shape or weight of the stock items requires that the partition portion 144 provide an increased resistance to becoming dislodged from the base portion 146. Securely attached to the pedestal 148 of the partition portion 144 is an oversized shoe-like member 150 that fits over and around the base portion 146, such that the base portion 146 is nested within the shoe-like member 150. A magnet (not shown) is located within the interior of the shoe-like member 150 and magnetically engages the metal catch member 152 in the base portion 146 as already described. In this manner, the partition portion 144 is provided a wider base and, hence, greater resistance against forces (like the weight of the stock items) that would otherwise tend to dislodge the partition portion 144 from the base portion 146 undesirably. In all other respects, the partition portion 144 functions in the manner previously discussed.

Still other exemplary embodiments of an inventory storage module of the present disclosure are shown in FIGS. 17A-19B. In these configurations, the storage module does not include a control portion that automatically broadcasts a restocking request, as previously described. Instead, the need to restock the storage module arises from a visual indication to the users and/or materials management personnel provided by the position of the sleeve in the storage bin. When the sleeve is relocated from the rear section of the storage bin to the front section of the storage bin, the clear meaning to the users of the system is that the first quantity of stock items has been depleted and action is needed to restock the storage module. Similarly, when the sleeve is located at the rear portion of the storage bin, this visual indicia to the users of the system means that the storage module does not need to be restocked.

As shown in FIGS. 17A-17C, the storage module 154 comprises a storage bin or tray 156 with a sliding sleeve 158 that segregates the two quantities of the stock item. When the first quantity 157 of stock is depleted, the user slides the sleeve 158 forward to access the second quantity 159 of stock. The position of the sleeve 158 visually signals to the user that restocking is required. During restocking, then, materials management personnel lifts and moves the sleeve 158, e.g., back to the rear section 161 of the storage bin and restocks the storage module 154 by placing stock items within the sleeve 158. In addition to the position of the sleeve 158, other visual indicia, like colors and labels on the bins or trays 156 and/or sleeves 158 can also be used to convey the need for restocking the storage module 154.

With particular reference to FIG. 17C, exemplary storage modules 154 of the inventory management system 10 can comprise a plurality of individual bins or trays 156 that can be closely arranged adjacent to one another to fit on a shelf or rack 160, for example. Each bin 156 may include vertical side walls 162 along which a sleeve 158 is positioned to slide within the bin 156. Alternatively, as shown in FIGS. 18A and 18B, the storage module 155 can comprise a large bin or tray 164 that may encompass the space on an entire shelf or rack 160. A plurality of adjustable, vertical side walls 166 can then be arranged in any of a variety of configurations to accommodate different types, sizes and/or quantities of stock, for example. In FIGS. 18A and 18B, the tray 164 is shown to include a plurality of horizontally spaced, vertical slots 168 that are operable to receive a corresponding tab 170 forming part of the side wall 166. The vertical side walls 166 can then be placed at different horizontal locations within the tray 164 to create a variety of sized compartments.

FIGS. 19A and 19B show still another storage module configuration 172. Similar to the storage module 154 shown in FIG. 17A, the storage module 172 of FIGS. 19A and 19B includes a pivotable lid 174 attached to the sleeve 176 that segregates the first quantity 178 of stock items from the second quantity 180 of stock items. As shown in FIGS. 19A and 19B, in the fully-stocked condition the sleeve 176 segregates the second quantity 180 of stock items located at the rear section 161 of the bin 156 from the first quantity 178 of stock items. In this condition, the lid 174 is positioned over the second quantity 180 of stock in a stowed position, thereby inhibiting access to the second quantity 180 of stock. After the first quantity 178 of stock has been depleted, the sleeve 176, together with the second quantity 180 of stock, is moved (e.g., slid) forward in the bin 156. The lid 174 can then be pivoted to a deployed position such that it no longer obstructs access to the second quantity 180 of stock. In the example shown, the deployed position of the lid 174 occurs when the lid 174 is pivoted approximately 270 degrees such that it is positioned over a front face 182 of the bin 156. Consequently, the position of the sleeve 176 (e.g., at the front of the bin 156) and the lid 174 being in the deployed position provides users of the system with the feedback prompting a restocking of the storage module 172, as necessary. Alternatively, or in addition, indicia visible on the deployed lid 174, or an audible signal during deployment of the lid 174, can also prompt a user to restock the storage module 172.

During restocking, then, the sleeve 176 is moved to the back section 161 of the bin 156 and the stock items that replenish the storage module 172 are placed within the confines of the containment portion 184 of the sleeve 176. In one aspect of the storage module 172, the lid 174 can also serve as a handle that can be grasped by a user of the system to assist in moving or manipulating the sleeve 176. In another aspect, the vertical walls 162 of the bin 172 and the lid 174 of the sleeve 176 may be cooperatively configured to prevent the lid 174 from pivoting except when the sleeve 176 has been repositioned forward in the bin. For example, the vertical walls 162 may each include a ledge portion 186 (FIG. 19A) which extends for a distance along the length of the rearward portion of the bin 156, and inwardly toward the bin's interior. The lid 174, when stowed, is positioned beneath the ledge 186 such that the ledge 186 obstructs any vertical movement of the lid 174 and prevents it from rotating. When the sleeve 176 is moved forward in the bin 156, however, the lid 174 is no longer beneath the ledge 186 and, consequently, it can be pivoted to the deployed position.

As discussed above, the inventory management system of the present disclosure may also include a data reader module 14. The data reader module 14 receives the signals from the storage modules 12 and provides the information to the data management module 16. The data reader module 14 can be associated with one or more storage locations containing tens, hundreds or thousands of individual storage modules 12. The data reader module 14 listens for restocking request broadcasts from the storage modules 12 with which it is associated. Upon detecting a restocking request, the data reader module 14 passes the request to the data management module 16 for further processing.

The data reader module 14 is coupled or networked to both the storage module 12 and the data management module 16 according to well-known communication protocols. The data reader module 14 is generally located remotely from and intermediate to, each of the storage module(s) 12 and the data management module 16. Depending upon the configuration or size, for example, of a particular managed operation, however, the functionality of the data reader module 14 may be subsumed within the operational capabilities of the data management module 16. Therefore, a separate data reader module 14 may be omitted from the system 10.

The data reader module 14 can be further understood with reference to FIGS. 20A, 20B and 21. Referring to FIGS. 20A, 20B and 21, the data reader module 14 comprises a body structure 188 including a base cover 190 and a base plate. The body structure 188 houses a computer module 192, such as a microprocessor, a memory module 194, a communications port 196 and a power supply 198. The computer module 192 can comprise a programmable or programmed device having memory, and may comprise or be coupled to a transceiver 200 and an antenna 202 that are operable to generate, receive and/or broadcast radio frequency (RF) signals, including RF signals containing information about the identity and/or condition of the storage module(s) that it monitors and/or the stock items contained therein. In addition, the communications port 196 of the data reader module 14 enables it to communicate with the data management module 16 according to well-known protocols over a local area network or the internet, for example.

Figure 24:
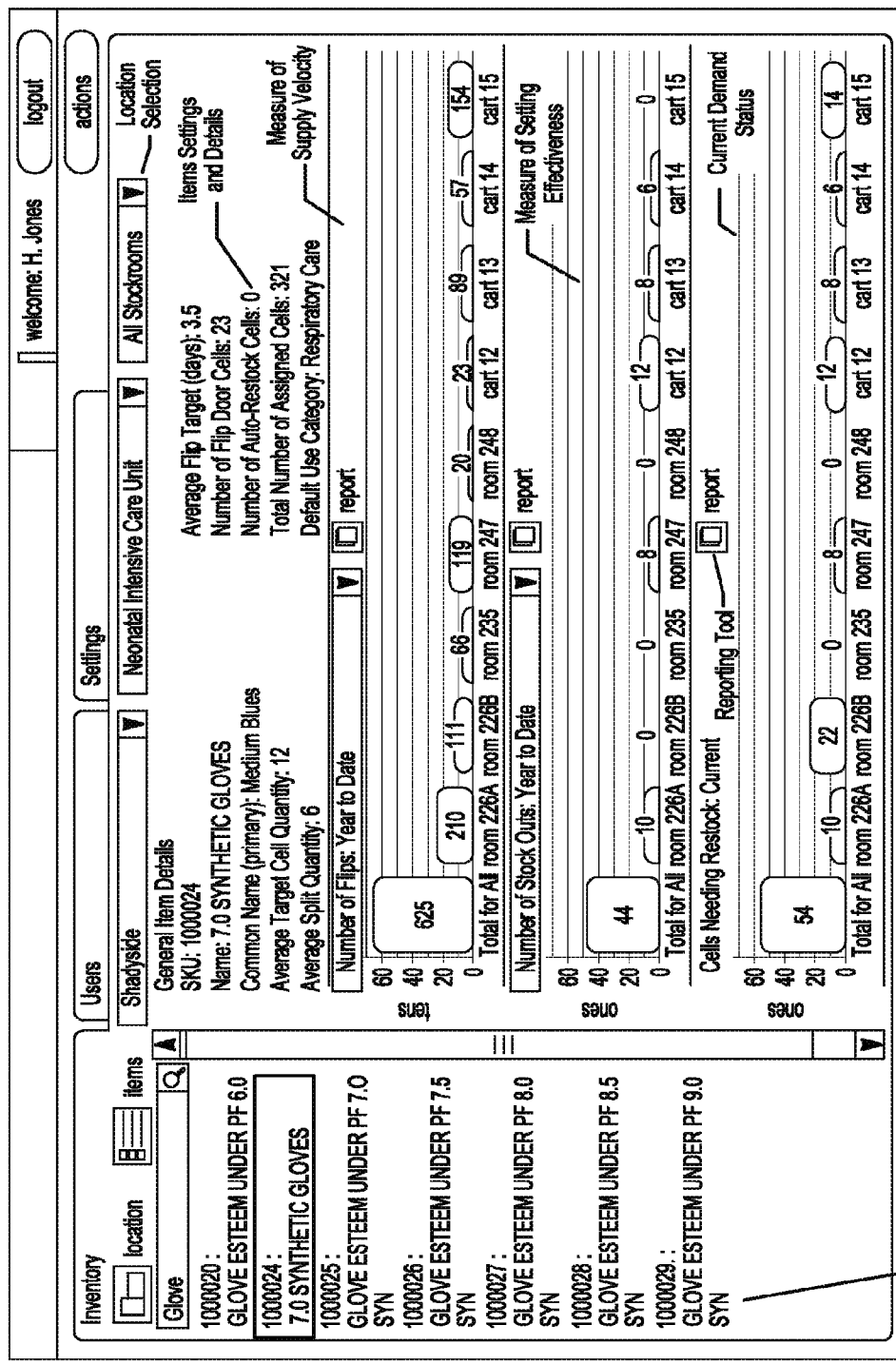
Figure 25:
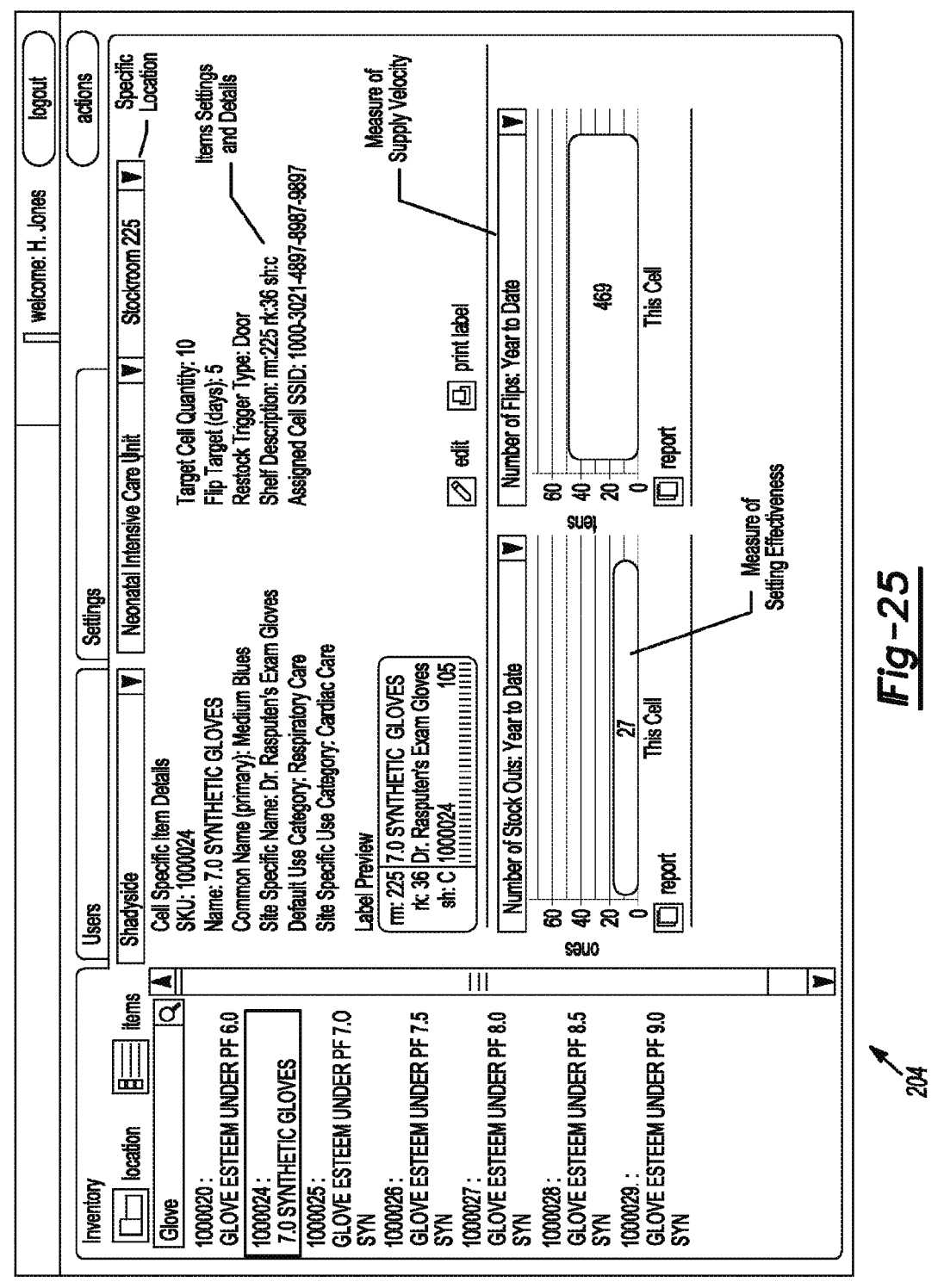
Figure 27:
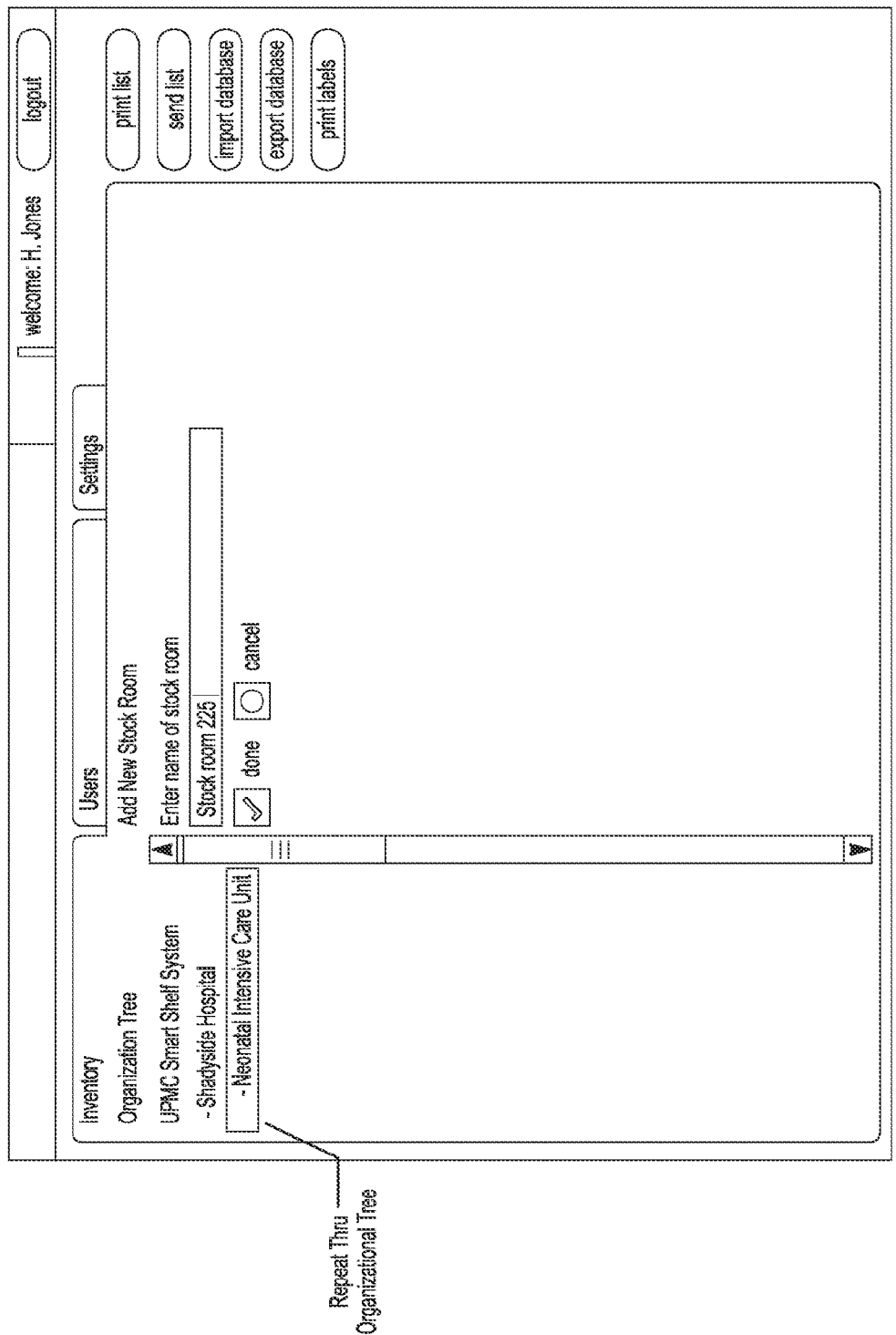

Referring to FIGS. 22-29, features and aspects of a data management module 16 for the inventory management system 10 are disclosed and described. In one aspect of the data management module 16 shown in FIGS. 22-25, a materials management interface 204 to the inventory management system 10 is provided. The interface 204 enables materials management personnel to monitor, track, and administer the stock items of inventory in real time, and at any and/or all of one or multiple locations and/or facilities in a managed organization or environment. For example, as shown in FIGS. 22-25, a variety of metrics relating to the managed inventory, including current demand status, supply velocity, item usage statistics, and setting effectiveness are easily seen on a single information screen. Particular inventory information more specific to a facility within a managed organization, or even to an individual storage location within a facility, is also easily accessed as seen, for example, in FIG. 24. Still further, metrics for individual inventory items are accessible on an item-by-item basis for individual managed locations, FIG. 25, or across multiple managed locations, as shown in FIG. 24. A report generator function (see FIG. 24) included in the interface 204 enables the inventory management system 10 to produce any records relating to the managed inventory that may be necessary. Moreover, the metrics tracked by the inventory management system 10 may advantageously inform the managed organization's purchasing decisions for the stocked supplies.

With reference to FIGS. 26-29, various systems settings in the inventory management system can provide a managed organization the flexibility to customize the kinds of inventory-related information it tracks (see, e.g., FIGS. 26 and 28), the benchmarks against which certain metrics may be measured, the users that are authorized within the system (see, e.g., FIG. 29), and preferred naming conventions for stock (see, e.g., FIG. 28), locations and facilities (see, e.g., FIG. 27), among other features.

Figure 26:
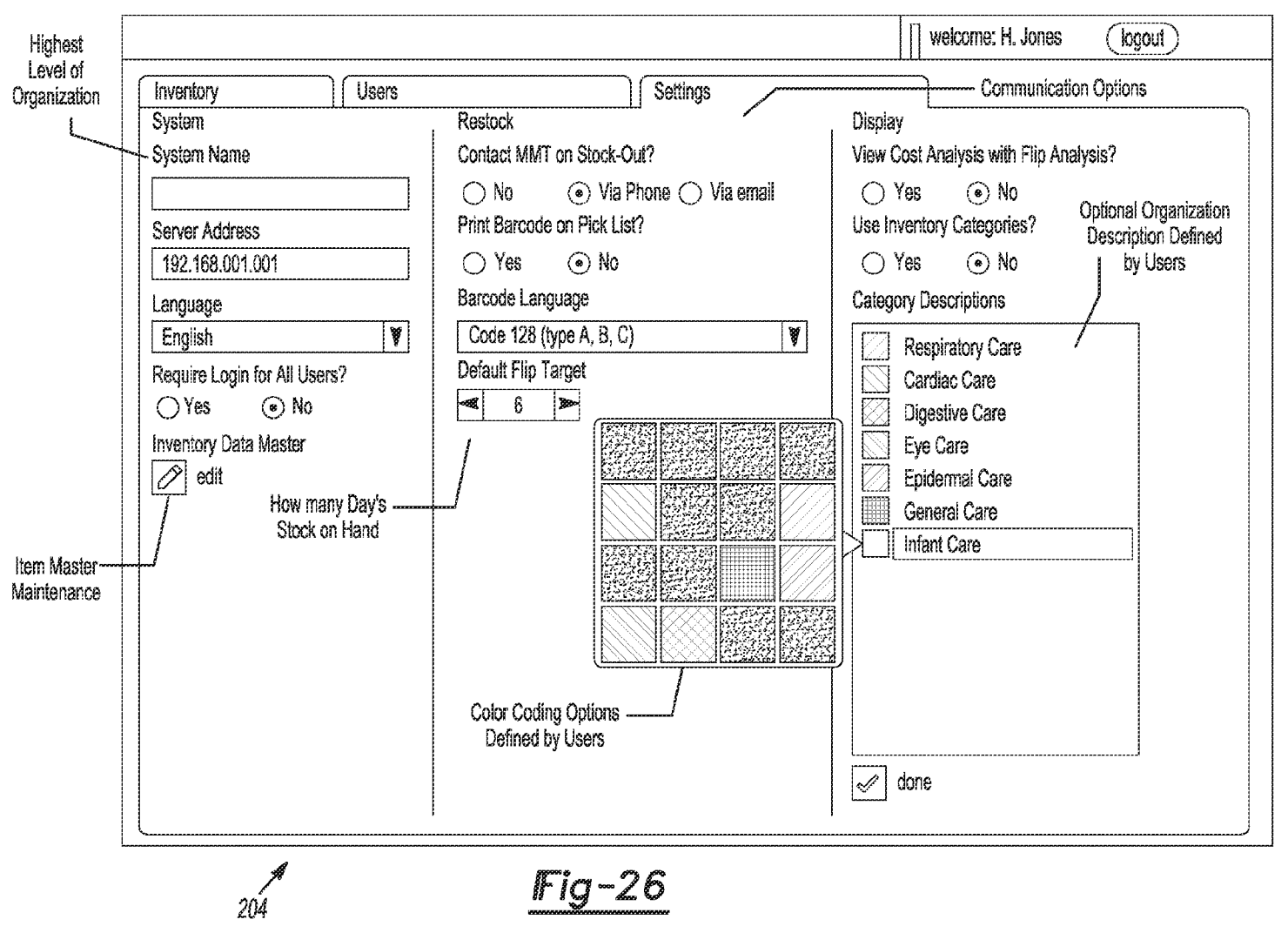

Another feature of the inventory management system is the ability to produce customized storage bin labels. As shown in FIGS. 26 and 28, for example, as information pertaining to a stock item is added within the system, a real time visualization of a bin label is provided. The label may include bar coding, color coding, as well as clinical and common names for the stock item.

Although the label for each stock item is customized, the system nevertheless maintains a uniform label format that promotes consistency from item-to-item, storage bin-to-storage bin, across all of the facilities and storage locations in a managed organization. Moreover, labeling uniformity helps reduce errors caused by improperly stocked or re-stocked inventory items.

Yet another embodiment of an inventory management system 10 according to the disclosure is understood with reference to FIGS. 30A, 30B and 31A-31C. This embodiment of the inventory management system 10 generally comprises a multi-bin system that incorporates radio frequency identification (RFID) functionality to automate a request to restock inventory. Referring to FIG. 30A, the system generally comprises a plurality of individual inventory storage modules 206 that are arranged on, for example, a storage shelf or rack device 208 or other suitable storage/dispensing platform for receiving the plurality of storage modules 206. Each storage module 206 comprises a storage bin 209 for containing inventory stock items and a passive RFID tag 210 that is associated with the storage module 206 in the inventory management system 10. The RFID tag 210 provides unique identifying information relating to the storage module 206. A corresponding RFID antenna/reader 212 is included in the system and may, for example, be integrated into a portion of the storage platform 208 on which the storage modules 206 are arranged. The RFID antenna/reader 212 is operable to read the RFID tag 210 information of a storage module 206 when the storage module 206 is placed in proximity to the antenna/reader 212 and broadcast the information to, for example, a data reader module.

Referring again to the figures, exemplary arrangements of the inventory management system are shown. As illustrated in FIG. 30A, a storage rack device 208 includes a plurality of shelves 214 for receiving a plurality of the storage modules 206 which are normally supplied with stock items. The storage modules 206 are shown to be placed on the shelves 214 to maximize the capacity of the storage rack device 208, such as in a plurality of columns arranged in a side-by-side relationship to one another across the width of a shelf 214. Each column includes a plurality of storage modules 206 that are arranged in a row from the front to the back of the shelf 214. As such, the storage modules 206 are generally configured in a two-dimensional array (width×depth) on the shelf 214. Of course, the number of storage modules that may be included, the size and/or shape of the storage modules, and the particular arrangement of storage modules, can vary as desired or necessary. Moreover, the nature of the storage platform and the physical dimensions of the storage modules are completely variable and may be adapted to suit any requirement and still function within the inventory management system. Exemplary storage platforms can include carts, cabinets, workstations, or wall systems having drawers and/or shelves and/or work platforms, and the like.

Also, as shown in FIG. 30A, the RFID antenna/reader 212 is incorporated into and/or located at a separate section or portion of the storage platform 208. In the embodiment illustrated in FIG. 30A, the portion of the storage rack device 208 that is dedicated for the RFID antenna/reader 212 is a top shelf 215. The RFID antenna/reader 212 can, for example, be placed on the shelf as an overlay placed upon the surface of the shelf 215 or as an apparatus that is built directly into the shelf 215. Other options could include incorporating the RFID antenna/reader 212 into a mat that lays on a shelf or work surface, or a liner that is placed in a drawer. Alternatively, the RFID antenna/reader 212 can be incorporated directly into the features of a shelf, drawer or work surface of the storage platform, like a planar surface such as a wall, panel or platform.

FIG. 30A shows that the storage modules 206 are arranged in a ten columns wide by two rows deep two-dimensional array on the shelves 214 of the storage rack device 208. A first or front storage module in each of the columns serves as a primary storage module 216. The first storage module is placed directly in front of a second or rear storage module which serves as a secondary storage module 218. Therefore, the primary storage module 216 can be directly accessed by a user from the front side of the storage rack device 208, while direct access to the secondary storage module 218 is obstructed by the placement of the primary storage module. Of course, additional rows of storage modules (e.g., a third, fourth, fifth, etc.) may be included in some or all of the columns, and different quantities of storage modules and/or different sized storage modules may be included on the various shelves 214 of the storage rack device 208.

The primary 216 and secondary 218 storage modules 206 are initially supplied with stock items. As demands for the stock item occur during normal workflow, items are removed from the primary storage module 216 in a given column (which, at this point, is the first storage module) until the stock of items is depleted. When the last of the stock items is removed from the first storage module 216, the empty first storage module 216 is removed from the shelf 214 and placed at or on the section of the storage platform (in the embodiment shown at FIG. 30A, the top shelf 215 of the storage rack device 208) that incorporates the RFID antenna/reader 212. There, the RFID tag 210 included in the storage module 216 is read by the RFID reader/antenna 212 and a restocking request is broadcast RFID reader/antenna 212 to the data reader module 14 or inventory data management module 16, as previously described. With the first storage module 216 removed from the shelf 214, the second storage module 218 is relocated to occupy the position in the column that was previously occupied by the first storage module 216 and, as such, becomes the primary storage module. Then, additional demands for stock items are satisfied by stock contained in the second storage module 218. Meanwhile, the empty first storage module 216 is available to be restocked by materials management personnel. Thereafter, the now restocked first storage module 216 is placed on the shelf 214 in the former location of the second storage module 218; that is, in the column and behind the primary storage module which, at this point, is the second storage module 218. The cycle is then repeated as required.

As can be appreciated, the unique identifying information for the storage module that is contained in the RFID tag 210 enables the inventory data management module 16 of the inventory management system 10 to monitor compliance with "first in, first-out" (i.e., FIFO) stock consumption protocols, as necessary. For example, the restocking sequence for the first 216 and second 218 (and Nth) storage modules can be tracked in the system by including serialized identifiers (e.g., ID no. 1, 2, 3, N, etc.) for the related storage modules 206 (e.g., in each column). In this manner, the order in which the RFID tags 210 of the storage modules 206 for a given stock item are read can inform users of the system whether FIFO is being followed. Still further, the inventory management system 10 can monitor for a "stock out" situation by tracking whether the RFID tags 210 of all the storage modules for a given stock item have been read without an intervening restocking activity by materials management personnel. Also, the system accommodates adjustments to the inventory levels that most effectively utilize the inventory assets.

While the foregoing example describes an arrangement of storage modules placed one in front of another, where the front-most storage module is accessible and the storage modules behind are not, the inventory management system contemplated is equally applicable to an arrangement of a plurality of storage modules that are stacked one on top of another in an over-under relationship, such as shown in the example illustrated in FIG. 30B.

In addition, this exemplary embodiment of an inventory management system is easily adapted to accommodate stock items that cannot be conveniently housed within a bin of a storage module and/or on a storage/dispensing platform as has been described. For example, the system can be adapted for large items and/or hanging items with one or more identification card(s) incorporating a RFID tag, as shown in FIGS. 31A and 31B. As illustrated, for example, the RFID tagged identification card(s) 220 serves as a physical marker that can be placed on or among the stock items 222 (e.g., hanging with the stock items, or removeably affixed to the packaging of stock items). When the stock is removed, the card can be taken from among the items (or removed from the packaging) and placed at the location of the RFID reader/antenna (e.g., in a receptacle 224). The stock item's RFID tag information is then read and a restocking request is broadcast as previously described.

It is clear that the protocol utilized by the inventory management system described in the disclosure promotes a "first in, first out" consumption of stock. In this manner, waste and stock loss due to expiry are minimized. Moreover, since the same fixed quantity of an item is used for each restocking event, restocking operations are simplified as compared with PAR systems.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for managing an inventory of stock items comprising:

an inventory storage module comprising:

a storage bin adapted to contain a plurality of a stock item that are segregated into a first quantity of the stock item and a second quantity of the stock item, the first quantity of the stock item being located at a first position in the storage bin and the second quantity being located at a second position in the storage bin, wherein a first identification label is disposed on a front of the storage bin; and a sleeve received within an interior space of the storage bin, the sleeve comprising a control portion and a containment portion;

the control portion including a trigger that is movable between a first position and a second position, and a second identification label that is substantially the same as the first identification label, the control portion being operable to broadcast a radio frequency (RF) signal containing information relating to the identity or condition of the storage module;

the containment portion comprising a wall-like perimeter structure without a bottom enclosure, the containment portion defining an interior volume and adapted to segregate the second quantity of the stock item from the first quantity of the stock item within the storage bin; and wherein the inventory storage module broadcasts a restocking request upon movement of the trigger; and an inventory data management module comprising a user interface, the inventory data management module facilitating the administration of the stock items in the inventory based upon the restocking request.

2. The system of claim 1, further comprising a data reader module that receives the restocking signal from inventory storage module and transmits the restocking request to the data management module.

3. The system of claim 2 wherein the data reader module comprises a computer module, a communications port, a transceiver and an antenna.

4. The system of claim 3 wherein the transceiver and antenna are operable to receive or broadcast radio frequency (RF) signals containing information about the condition of the storage module or the stock items contained therein.

5. The system of claim 2 wherein the data reader module is associated with a plurality of storage modules.

6. The system of claim 2 wherein the data reader module is networked to both the storage module and the data management module.

7. The system of claim 1 wherein the control portion further comprises an indicator of the status of the storage module as being in the restocking condition.

8. The system of claim 1 wherein the control portion comprises a computer module, a sensor, a transceiver and an antenna; and wherein the sensor detects movement of the trigger.

9. A system for managing an inventory of stock items comprising:

an inventory storage module comprising:
a divider member attached directly to a shelf of a storage device that is adapted to hold a plurality of a stock item that are segregated into a first quantity of the stock item and a second quantity of the stock item, the first quantity of the stock item being located at a first position on the storage device and the second quantity being located at a second position on the storage device;

the divider member comprising a base portion and a trigger device, the trigger device being pivotable between a first position where the trigger device obscures one of the first or second quantities of the stock item, and a second position;

the base portion being operable to detect movement of the trigger and to broadcast a radio frequency (RF) signal containing information relating to the identity or condition of the storage module; and an inventory data management module comprising a user interface, the inventory data management module facilitating the administration of the stock items in the inventory based upon the identity or condition of the storage module.

10. The system of claim 9 wherein the base portion comprises a computer module, a sensor, a transceiver and an antenna; and wherein the sensor detects movement of the trigger; and
wherein the inventory storage module broadcasts a restocking request upon movement of the trigger.

11. The system of claim 10 wherein the restocking request is transmitted to the inventory data management module.

12. The system of claim 10, further comprising a data reader module that receives the restocking signal from inventory storage module and transmits the restocking request to the data management module.

13. The system of claim 12 wherein the data reader module is associated with a plurality of storage modules.

14. The system of claim 12 wherein the data reader module comprises a computer module, a communications port, a transceiver and an antenna.

15. The system of claim 14 wherein the transceiver and antenna are operable to receive or broadcast radio frequency (RF) signals containing information about the condition of the storage module or the stock items contained therein.

16. A system for managing an inventory of stock items comprising:

an inventory storage module comprising:
a storage bin adapted to contain a plurality of a stock item that are segregated into a first quantity of the stock item and a second quantity of the stock item, the first quantity of the stock item being located at a first position in the storage bin and the second quantity being located at a second position in the storage bin;

a divider member received within an interior space of the storage bin, the divider member separating the first quantity of the stock item from the second quantity of the stock item, the divider member comprising a base portion and a partition portion, the partition portion comprising a trigger that is movable between a first position and a second position, the base portion being operable to detect movement of the trigger and to broadcast a radio frequency (RF) signal containing information relating to the identity or condition of the storage module; and an inventory data management module comprising a user interface, the inventory data management module facilitating the administration of the stock items in the inventory based upon the identity or condition of the storage module.

17. The system of claim 16 wherein the base portion comprises a computer module, a sensor, a transceiver and an antenna;

wherein the sensor detects movement of the trigger; and
wherein the inventory storage module broadcasts a restocking request upon movement of the trigger.

18. The system of claim 17 wherein the restocking request is transmitted to the inventory data management module.

19. The system of claim 17, further comprising a data reader module that receives the restocking signal from inventory storage module and transmits the restocking request to the data management module.

20. The system of claim 19 wherein the data reader module comprises a computer module, a communications port, a transceiver and an antenna.

21. The system of claim 20 wherein the transceiver and antenna are operable to receive or broadcast radio frequency (RF) signals containing information about the condition of the storage module or the stock items contained therein.

22. The system of claim 19 wherein the data reader module is associated with a plurality of storage modules.

* * * * *